(12) United States Patent
Jeong et al.

(10) Patent No.: US 10,223,381 B2
(45) Date of Patent: Mar. 5, 2019

(54) SENSOR INFORMATION USING METHOD AND ELECTRONIC DEVICE USING THE SAME

(71) Applicant: Samsung Electronics Co., Ltd., Gyeonggi-do (KR)

(72) Inventors: Seong Ook Jeong, Gyeonggi-do (KR); Jong Kun Lee, Gyeonggi-do (KR); Seung Wok Han, Seoul (KR); Kyung Sub Min, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 248 days.

(21) Appl. No.: 15/159,948

(22) Filed: May 20, 2016

(65) Prior Publication Data
US 2016/0342622 A1    Nov. 24, 2016

(30) Foreign Application Priority Data
May 21, 2015   (KR) .................. 10-2015-0071040

(51) Int. Cl.
G06F 19/00     (2018.01)
G06F 3/0484    (2013.01)
H04W 4/02      (2018.01)
G06F 17/30     (2006.01)
G09B 29/10     (2006.01)
(Continued)

(52) U.S. Cl.
CPC ....... *G06F 17/30241* (2013.01); *G01C 21/20* (2013.01); *G01C 22/006* (2013.01); *G06F 3/0484* (2013.01); *G06F 17/3087* (2013.01); *G06F 19/00* (2013.01); *G06F 19/3481* (2013.01); *G09B 29/106* (2013.01); *H04W 4/02* (2013.01); *G01S 19/19* (2013.01); *G09B 29/007* (2013.01); *H04W 4/027* (2013.01); *H04W 4/80* (2018.02)

(58) Field of Classification Search
CPC .............................. G04F 10/00; G01C 22/006
USPC .................................. 715/763–765, 851–853
See application file for complete search history.

(56) References Cited

U.S. PATENT DOCUMENTS 6,212,469 B1   4/2001   Knepper
7,397,365 B2   7/2008   Wang
(Continued)

FOREIGN PATENT DOCUMENTS

| EP | 2 581 120 A1 | 4/2013 |
| WO | 2006/065679 A2 | 6/2006 |
| WO | 2012/021507 A2 | 2/2012 |

OTHER PUBLICATIONS

International Search Report dated Sep. 6, 2016.
European Search Report dated Oct. 19, 2016.

*Primary Examiner* — Cao H Nguyen
(74) *Attorney, Agent, or Firm* — Cha & Reiter, LLC.

(57) ABSTRACT

An electronic device in response to an embodiment of the present disclosure includes a non-transitory memory configured to store at least one executable instruction and at least one processor connected to the memory. The at least one processor is configured by executing the instruction to calculate a distance traveled based on collected sensor information received from a plurality of sensors in response to detecting movement of the electronic device, to divide the calculated distance traveled by a specified reference unit, and output a specified object to a region including at least one reference unit point.

20 Claims, 14 Drawing Sheets

(51) Int. Cl.
  *G01C 21/20* (2006.01)
  *G01C 22/00* (2006.01)
  *G09B 29/00* (2006.01)
  *H04W 4/80* (2018.01)
  *G01S 19/19* (2010.01)

(56) References Cited

U.S. PATENT DOCUMENTS

| | | | |
|---|---|---|---|
| 9,087,234 | B2 | 7/2015 | Hoffman et al. |
| 9,248,340 | B2* | 2/2016 | Hoffman ............ A63B 24/0084 |
| 9,341,494 | B2 | 5/2016 | Kosakowski et al. |
| 2006/0136173 | A1 | 6/2006 | Case, Jr. et al. |
| 2007/0115113 | A1 | 5/2007 | Wang |
| 2007/0287596 | A1 | 12/2007 | Case, Jr. et al. |
| 2009/0164115 | A1* | 6/2009 | Kosakowski ...... G01C 21/3641 701/533 |
| 2009/0319230 | A1 | 12/2009 | Case, Jr. et al. |
| 2010/0210421 | A1 | 8/2010 | Case, Jr. et al. |
| 2010/0331145 | A1* | 12/2010 | Lakovic ................. G04F 10/00 482/8 |
| 2011/0003665 | A1 | 1/2011 | Burton et al. |
| 2011/0007468 | A1 | 1/2011 | Burton et al. |
| 2011/0032105 | A1 | 2/2011 | Hoffman et al. |
| 2012/0078396 | A1 | 3/2012 | Case, Jr. et al. |
| 2012/0116550 | A1 | 5/2012 | Hoffman et al. |
| 2014/0046588 | A1 | 2/2014 | Maezawa et al. |
| 2014/0172132 | A1 | 6/2014 | Ura |
| 2014/0200847 | A1* | 7/2014 | Singiresu ............. G01C 22/006 702/141 |
| 2014/0228986 | A1 | 8/2014 | Case, Jr. et al. |
| 2014/0228987 | A1 | 8/2014 | Case, Jr. et al. |
| 2014/0228988 | A1 | 8/2014 | Hoffman et al. |
| 2014/0288680 | A1 | 9/2014 | Hoffman et al. |
| 2014/0330409 | A1 | 11/2014 | Case, Jr. et al. |
| 2015/0095336 | A1 | 4/2015 | Green et al. |
| 2015/0251053 | A1 | 9/2015 | Hoffman et al. |
| 2015/0258380 | A1 | 9/2015 | Hoffman et al. |
| 2015/0306457 | A1 | 10/2015 | Crankson et al. |
| 2015/0338236 | A1 | 11/2015 | Hoffman et al. |
| 2016/0107064 | A1 | 4/2016 | Hoffman et al. |
| 2016/0121163 | A1 | 5/2016 | Case, Jr. et al. |

* cited by examiner

SENSOR INFORMATION USING METHOD AND ELECTRONIC DEVICE USING THE SAME

CLAIM OF PRIORITY

This application claims the benefit of priority under 35 U.S.C. § 119(a) from a Korean patent application filed on May 21, 2015 in the Korean Intellectual Property Office and assigned Serial number 10-2015-0071040, the entire disclosure of which is hereby incorporated by reference.

BACKGROUND

1. Field of the Disclosure

The present disclosure relates to use of sensor information.

2. Description of the Related Art

Electronic devices are used to support various user functions. For example, electronic devices may be used to support an exercise measurement function. Moreover, the electronic devices may support the exercise measurement function based on information collected by a global positioning system (GPS) sensor.

The GPS sensor may collect location information of an electronic device using a satellite. The GPS sensor may have a certain error rate depending on a surrounding environment. For example, in the case where an electronic device equipped with the GPS sensor enters a building, GPS information may be unable to be received. The GPS sensor may provide incorrect location information due to a surrounding electronic environment. Therefore, in the case where the exercise measurement function is provided based on GPS information alone, incorrect information may be provided, and there is a need to improve the accuracy of such electronic devices, particularly when operated in areas such as building where the receipt of GPS may not be received.

SUMMARY

Accordingly, an aspect of the present disclosure is to provide a sensor information more accurately than known heretofore. Therefore, the disclosure provides a sensor information using method for collecting more accurate sensor information and providing a reliable exercise measurement function based on the sensor information and an electronic device using the same.

In accordance with an aspect of the present disclosure, an electronic device is provided. The electronic device includes a memory configured to store at least one instruction configured to output information in response to execution of an exercise function, and a at least one processor connected to the memory, wherein the instruction executed by the at least one processor is configured to calculate a distance traveled based on portions of sensor information received from a plurality of sensors for collecting sensing information when the electronic device is moving (e.g. a movement state), divide the calculated distance traveled by a specified reference unit, and output a specified object to a screen region including at least one reference unit point.

In accordance with another aspect of the present disclosure, a sensor information using method is provided. The sensor information using method includes collecting at least a portion of sensor information according to a movement state using a plurality of sensors, calculating a distance traveled based on collected portions of sensor information, dividing the calculated distance traveled by a specified reference unit, and outputting a specified object to a screen region including at least one reference unit point.

DETAILED DESCRIPTION

Figure 1:
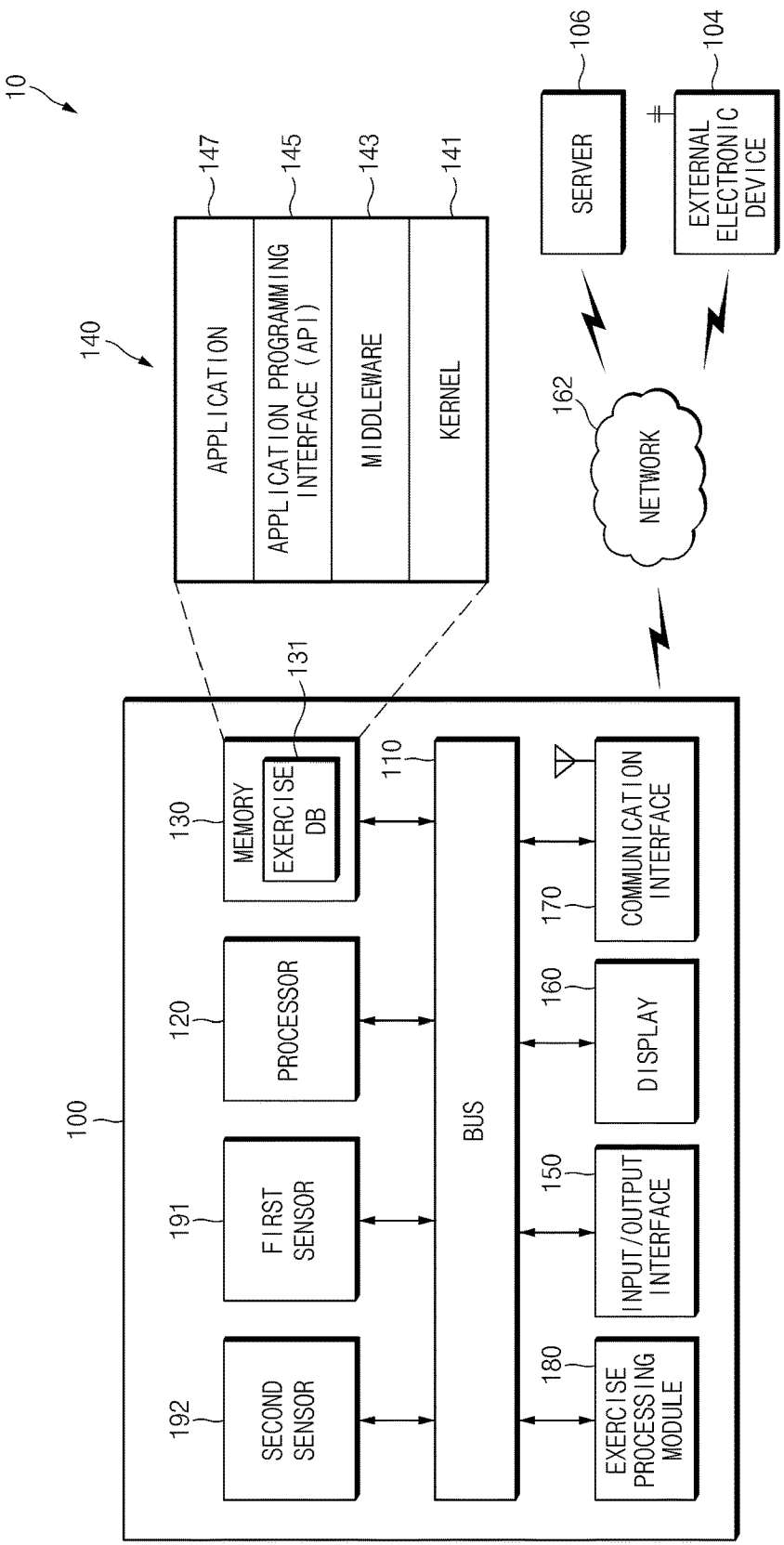
FIG. 1 is a diagram illustrating an example of an electronic device operating environment according to an embodiment of the present disclosure.

Hereinafter, various embodiments of the present disclosure will be described in detail with reference to the accompanying drawings. However, it should be understood that the scope of the appended claims is not limited to specific embodiments, but rather includes various modifications, equivalents and/or alternatives of various embodiments of the present disclosure. Regarding description of the drawings, like reference numerals may refer to like elements.

The term "have", "may have", "include", "may include", "comprise", or the like used herein indicates the existence of a corresponding feature (e.g., a number, a function, an operation, or an element) and does not exclude the existence of an additional feature.

The term "A or B", "at least one of A and/or B", or "one or more of A and/or B" may include all possible combinations of items listed together. For example, the term "A or B", "at least one of A and B", or "at least one of A or B" may indicate all the cases of (1) including at least one A, (2) including at least one B, and (3) including at least one A and at least one B.

The term "first", "second" or the like used herein may modify various elements regardless of the order and/or priority thereof, but does not limit the elements. For example, "a first user device" and "a second user device" may indicate different user devices regardless of the order or priority. For example, without departing the scope of the present disclosure, a first element may be referred to as a second element and vice versa.

It will be understood that when a certain element (e.g., a first element) is referred to as being "operatively or communicatively coupled with/to" or "connected to" another element (e.g., a second element), the certain element may be coupled to the other element directly or via another element (e.g., a third element). However, when a certain element (e.g., a first element) is referred to as being "directly coupled" or "directly connected" to another element (e.g., a second element), there may be no intervening element (e.g., a third element) between the element and the other element.

The term "configured (or set) to" used herein may be interchangeably used with the term, for example, "suitable for", "having the capacity to", "designed to", "adapted to", "made to", or "capable of". The term "configured (or set) to" may not necessarily have the meaning of "specifically designed to". In some cases, the term "device configured to" may indicate that the device "may perform" together with other devices or components. For example, the term "processor configured (or set) to perform A, B, and C" may represent a dedicated processor (e.g., an embedded processor) for performing a corresponding operation, or a generic-purpose processor (e.g., a CPU or an application processor) for executing one software program stored in a memory device to perform a corresponding operation.

The terminology used herein is only used for describing specific embodiments and is not intended to limit the scope of claims directed to other embodiments. The terms of a singular form may include plural forms unless otherwise specified. The terms used herein, including technical or scientific terms, have the same meanings as understood by those skilled in the art. Commonly-used terms defined in a dictionary may be interpreted as having meanings that are the same as or similar to contextual meanings defined in the related art, and should not be interpreted in an idealized or overly formal sense unless otherwise defined explicitly. Depending on cases, even the terms defined herein should not be such interpreted as to exclude various embodiments of the present disclosure.

An electronic device according to various embodiments of the present disclosure varies widely in application and may include at least one of a smartphone, a tablet personal computer (PC), a mobile phone, a video telephone, an electronic book reader, a desktop PC, a laptop PC, a netbook computer, a workstation, a server, a personal digital assistant (PDA), a portable multimedia player (PMP), a Motion Picture Experts Group (MPEG-1 or MPEG-2) Audio Layer 3 (MP3) player, a mobile medical device, a camera, or a wearable device (e.g., smartglasses, a head-mounted device (HMD), an electronic apparel, an electronic bracelet, an electronic necklace, an electronic appcessory, an electronic tattoo, a smart mirror, or a smartwatch).

Hereinafter, an electronic device according to various embodiments of the present disclosure will be described with reference to the accompanying drawings. The term "user" used herein may refer to a person who uses an electronic device or may refer to a device (e.g., an artificial electronic device) that uses an electronic device.

FIG. 1 is a diagram illustrating an example of an electronic device operating environment according to an embodiment of the present disclosure.

Referring now to FIG. 1, an operation environment 10 in which an electronic device 100 is operated may include the electronic device 100, a network 162, and an external electronic device 104.

In the electronic device operating environment 10, the electronic device 100 may collect sensor information by operating a plurality of sensors 191 and 192, and may process information associated with an exercise function based on the collected sensor information. According to an embodiment of the present disclosure, the electronic device 100 may determine a distance traveled based on at least a portion of sensor information collected by the first sensor 191 (e.g., a GPS sensor) and the second sensor 192 (e.g., a pedometer) associated with movement sensing, and may obtain coordinate information (e.g., GPS coordinate information) corresponding to a specified reference unit point (or reference unit position, or reference unit spot, or reference unit location). The electronic device 100 may output a specified first object (e.g., a marking point or the like indicating passing through the reference unit point). In the case where the coordinate information corresponding to the reference unit point is unable to be obtained, the electronic device 100 may output a specified second object (e.g., a line representing a certain section including the reference unit point) corresponding to a distance traveled including the reference unit point. In the case where an exercise is ended while the coordinate information corresponding to the reference unit point is unable to be obtained, the electronic device 100 may output a third object (e.g., an image having a specified shape such as a flag or the like) corresponding to the end of the exercise. Furthermore, the electronic device 100 may output, to a display 160, a fourth object (e.g., a line or the like having a specified color or width) associated with a moving speed.

With regard to detection of the reference unit point, the electronic device 100 may collect user real-time information complexly sensed (or compensated) as shown in table 1 and user location information (e.g., GPS information) as shown in table 2.

TABLE 1

| Time | Speed | Distance difference | ... |
|------|-------|---------------------|-----|
| 11:50:10 | 1.98 m/s | 16.0 m | ... |
| 11:50:14 | 2.12 m/s | 7.0 m | ... |
| 11:50:20 | 0.47 m/s | 20.0 m | ... |
| ... | ... | ... | ... |
| 12:00:10 | 2.42 m/s | 6.0 m | ... |
| 12:00:15 | 1.29 m/s | 9.0 m | ... |
| 12:00:20 | 1.5 m/s | 8.0 m | ... |

TABLE 2

| Time | Latitude | Longitude | Altitude | ... |
|---|---|---|---|---|
| 11:50:10 | 37.26164 | 127.05405 | −53.553608 | ... |
| 11:50:14 | 37.261192 | 127.054565 | −54.478405 | ... |
| 11:50:20 | 37.26067 | 127.054344 | −53.22068 | ... |
| ... | ... | ... | ... | ... |
| 12:00:10 | 37.26103 | 127.05359 | −54.34629 | ... |
| 12:00:14 | 37.26069 | 127.05254 | −54.245884 | ... |
| 12:00:20 | 37.257946 | 127.05045 | −54.45198 | ... |

In the above information, the electronic device 100 may obtain time information corresponding to the reference unit point, such as 12:00:10, in table 1. Accordingly, the electronic device 100 may detect location information (37.26103, 127.05359) corresponding to the time information 12:00:10 in table 2. The electronic device 100 may determine the location information (37.26103, 127.05359) as the reference unit point, and may output a specified object (e.g., an object in which number information indicating the reference unit point is written) to a corresponding location.

The network 162 may support establishment of a wireless communication channel among the first electronic device 100, the external electronic device 104, and the server 106. In addition, in the case where the external electronic device 104 includes a wireless communication interface, the network 162 may support establishment of a wireless communication channel of the external electronic device 104. The network 162 may include at least one device element capable of supporting a wireless communication function (e.g., various wireless communication standards such as 2G, 3G, 4G, LTE, 5G, etc.), a wireless access communication function (e.g., a Wi-Fi communication function), etc. The network 162 may include at least one of telecommunications networks, for example, a computer network (e.g., a LAN or WAN), the Internet, or a telephone network. The network 162 may support establishment of a communication channel between the server 106 or the external electronic device 104 and the electronic device 100. According to an embodiment of the present disclosure, the network 162 may transfer, to the server 106 or the external electronic device 104, exercise function-related information collected by the electronic device 100.

The server 106 may be connected to the electronic device 100 via the network 162. For example, the server 106 may establish a wireless communication channel in response to a request from the electronic device 100. The server 106, for example, may receive specific data from the electronic device 100. Furthermore, the server 106 may transmit specific data to the electronic device 100. According to an embodiment of the present disclosure, the server 106 may receive, from the electronic device 100, exercise function-related information (e.g., information on an exercise analytic quantity, a traveled distance, or a moving speed associated with an exercise). The server 106 may store and manage the exercise function-related information for each user information registered by a user or identification information of the electronic device 100. The server 106 may provide the stored exercise function-related information to the electronic device 100 in response to a request from the electronic device 100 or may transmit the stored exercise function-related information to another specified server.

The type of the external electronic device 104 may be the same as or different from that of the electronic device 100. According to various embodiments of the present disclosure, a portion or all of operations performed in the electronic device 100 may be performed in one or more other electronic devices (e.g., the external electronic device 104 or the server 106). According to another embodiment of the present disclosure, in the case where the electronic device 100 should perform a certain function or service automatically or in response to a request, the electronic device 100 may request at least a portion of functions associated with the function or service from another device (e.g., the external electronic device 104 or the server 106) instead of or in addition to performing the function or service for itself. The other electronic device (e.g., the external electronic device 104 or the server 106) may perform the requested function or additional function, and may transfer a result of the performance to the electronic device 100. The electronic device 100 may intactly use or additionally process a received result to provide the requested function or service. To this end, for example, a cloud computing technology, a distributed computing technology, or a client-server computing technology may be used. FIG. 1 illustrates that the external electronic device 104 is connected via the network 162, but various embodiments of the present disclosure are not limited thereto. For example, the external electronic device 104 may be connected to the electronic device 100 via a short-range communication channel.

According to various embodiments of the present disclosure, the external electronic device 104 may comprise a companion device of the electronic device 100. The external electronic device 104 may store the exercise function-related information received from the electronic device 100. Furthermore, the external electronic device 104 may output the exercise function-related information received from the electronic device 100. According to various embodiments of the present disclosure, the external electronic device 104 may include a first sensor (e.g., a GPS sensor) and a second sensor (e.g., a pedometer sensor). The external electronic device 104 may provide, to the electronic device 100, sensor information collected by the first and second sensors. In relation to this operation, the external electronic device 104 may establish a short-range communication channel to the electronic device 100.

The electronic device 100 may include a bus 110, at least one processor 120, a non-transitory memory 130, an input/output interface 150, the display 160, a communication interface 170, and an exercise processing module 180. Furthermore, the electronic device 100 may include the first sensor 191 and the second sensor 192. According to various embodiments of the present disclosure, the first and second sensors 191 and 192 may be arranged in a companion device (e.g., the external electronic device 104) which establishes a short-range communication channel to the electronic device 100. In this case, the electronic device 100 may not be provided with the first and second sensors 191 and 192. Here, the electronic device 100 may receive first sensor information and second sensor information from the external electronic device 104 including the first and second sensors.

The bus 110 may include a circuit for connecting the above-mentioned elements 120 to 180, 191, and 192 to each other and transferring communications (e.g., control messages and/or data) among the above-mentioned elements.

The at least one processor 120, which comprises hardware circuitry such as integrated circuits, may include at least one of a central processor 120 may perform data processing or an operation associated with communication and/or control of at least one of the other elements of the electronic device 100. The at least one processor may be arranged as part of a controller or control unit. According to an embodiment of the present disclosure, the processor 120 may enable the first and second sensors 191 and 192 according to a user input or a scheduled setting.

According to an embodiment of the present disclosure, the at least one processor 120 may detect current location information of the electronic device 100 based on the first sensor information and the second sensor information collected by the first and second sensors 191 and 192. The at least one processor 120 may output, to the display 160, at least one of a first object (e.g., an object output as the reference unit point is passed), a second object (e.g., an object output when information on a current location does not exist after the reference unit point is passed), a third object (e.g., a specified object associated with an end of an exercise), or a fourth object associated with a moving speed according to a result of determining the current location information and a specified condition.

According to various embodiments of the present disclosure, the processor 120 may output, to the display 160, at least one of distance traveled information, section region information, synthetic exercise amount information, and analysis information analyzed based on collected portions of sensor information. The above-mentioned processor 120, for example, may correspond to at least a part of the exercise processing module 180. For example, at least one processor 120 may constitute the exercise processing module 180. Alternatively, at least a part of the processor 120 may constitute the exercise processing module 180.

The memory device 130 may include a volatile memory and/or a nonvolatile memory. The memory 130 may store instructions or data associated with at least one of the other elements of the electronic device 100. The instructions may be executed by the processor 120 or the exercise processing module 180. The instructions may include an instruction configured to enable at least one of the first sensor 191 or the second sensor 192, an instruction configured to collect at least one of the first sensor information or the second sensor information according to a situation, and an instruction for calculating a distance traveled based on at least one of the first sensor information or the second sensor information collected. Furthermore, the instructions may include an instruction for determining whether the calculated distance traveled satisfies a specified condition (e.g., passing through a specified reference unit point) and an instruction configured to output the first object as the specified condition is satisfied. Furthermore, the instructions may include an instruction to calculate a location at which the first sensor information has failed to be obtained and an instruction configured to output the second object according to a certain section including the calculated location. Furthermore, the instructions may include an instruction that configures the processor to recognize an end of an exercise before a specified distance is traveled, and instruction configured to output the specified third object in response to the end of the exercise, and an instruction configured to output the specified fourth object according to a moving speed.

According to various embodiments of the present disclosure, the memory 130 may store an exercise database 131. The exercise database 131 may include the first sensor information and first time information collected by the first sensor 191 and second time information, a moving speed, and distance traveled information calculated based on the first sensor information and the second sensor information collected by the first sensor 191 and the second sensor 192. The first time information and the second time information may be the same time information substantially synchronized. The information stored in the exercise database 131 may be used as reference information for outputting information to objects.

A moving speed value and a distance traveled difference may be accumulated and stored in the exercise database 131. Accordingly, a speed, a distance, and a time stamp may be additionally stored in the exercise database 131. Since a stored speed value may not match a time stamp value of a traveled distance, the electronic device 100 may search for a time stamp value corresponding to a desired distance using a user information table, and may select distance difference information associated with a closest time stamp to the time stamp value corresponding to the desired distance. The electronic device 100 may select a time stamp for a value which is closest to the reference unit point (e.g., 1 km position) when a distance difference is added. According to an embodiment of the present disclosure, in the case where information indicating 0.98 km at 15 minutes and 10 seconds and 1.05 km at 16 minutes is stored, the electronic device 100 may output an object for displaying the reference unit point using information obtained at 15 minutes and 10 seconds since a distance value of 15 minutes and 10 seconds is closer to the reference unit point.

Furthermore, the electronic device 100 may obtain location information of a user (or an electronic device) to display the reference unit point. When information of the time point of 15 minutes and 10 seconds is selected in the exercise database 131 (e.g., a speed and distance DB), the electronic device 100 may obtain coordinate information corresponding to the time point of 15 minutes and 10 seconds from a GPS database. According to various embodiments of the present disclosure, in the case where GPS coordinate information corresponding to the time point of 15 minutes and 10 seconds does not exist, but coordinate information of the time point of 15 minutes and 20 seconds and the time point of 14 minutes and 50 seconds exists in the GPS database, the electronic device 100 may select time information (e.g., GPS coordinate information of the time point of 15 minutes and 20 seconds) which relatively approximates to 15 minutes and 10 seconds. If pieces of time information (e.g., the time point of 15 minutes and the time point of 15 minutes and 20 seconds) which are prior to or follow the time point of 15 minutes s and 10 seconds are equally close to the time point of 15 seconds and 10 seconds, the electronic device 100 may randomly select either of the two portions of information or may select the prior information (or following information) according to a set policy. In the case where GPS coordinate information exists within a specified certain range with respect to a reference unit distance, the electronic device 100 may output an object (e.g., an image in which order information is written) corresponding to the reference unit point. In the case where there is no information (e.g., coordinate information corresponding to a position within a range of 0.8-1.2 km or GPS coordinate information corresponding to a period of 30 seconds prior to and 30 seconds after the time point of 15 minutes and 10 seconds) within a certain range (e.g., information within a certain range with respect to a 1-km reference unit point), the electronic device 100 may output a specified object (e.g., a line with a certain width or color including the reference unit point).

According to various embodiments of the present disclosure, the memory 130 may store software and/or a program 140. The program 140 may include, for example, a kernel 141, a middleware 143, an application programming interface (API) 145, and/or an application program (or an application) 147. At least a portion of the kernel 141, the middleware 143, or the API 145 may be referred to as an operating system (OS).

The kernel 141 may control or manage system resources (e.g., the bus 110, the processor 120, the exercise processing module 180, the memory 130, or the like) used to perform operations or functions of other programs (e.g., the middleware 143, the API 145, or the application program 147). Furthermore, the kernel 141 may provide an interface for allowing the middleware 143, the API 145, or the application program 147 to access individual elements of the electronic device 100 in order to control or manage the system resources.

The middleware 143 may serve as an intermediary so that the API 145 or the application program 147 communicates and exchanges data with the kernel 141. Furthermore, the middleware 143 may handle one or more task requests received from the application program 147 according to a priority order. For example, the middleware 143 may assign at least one application program 147 a priority for using the system resources (e.g., the bus 110, the processor 120, the exercise processing module 180, the memory 130, or the like) of the electronic device 100. For example, the middleware 143 may handle the one or more task requests according to the priority assigned to the at least one application program 147, thereby performing scheduling or load balancing with respect to the one or more task requests.

The API 145 may include an interface for allowing the application 147 to control functions provided from the kernel 141 or the middleware 143. The API 145 may include, for example, at least one interface or function (e.g., an instruction) for the purpose of file control, window control, image processing, character control, or the like.

The application 147 may include an exercise application. The exercise application may be a program designed to operate the exercise database 131, the above-mentioned instructions, etc. The instructions may include, for example, a routine for requesting enablement of the first and second sensors 191 and 192 and a routine for requesting output of at least one of the first object, the second object, the third object, or the fourth object based on the first sensor information and the second sensor information. Additionally or alternatively, the exercise application may include a routine configured to output, to the display 160, at least one of a map region for an exercise section, a section region according to an exercise distance, synthetic information on a total exercise amount, or analysis information obtained through exercise amount analysis.

The input/output interface 150 may serve to transfer an instruction or data input from a user or another external device to (an)other element(s) of the electronic device 100. Furthermore, the input/output interface 150 may output instructions or data received from (an)other element(s) of the electronic device 100 to the user or another external device. The input/output interface 150 may include, for example, at least one physical button or touch button or a touchpad or a touch screen. Furthermore, the input/output interface 150 may include a means for input by an electronic pen or the like. Moreover, the input/output interface 150 may include an audio device for processing audio signals. The audio device may output audio data associated with execution of the exercise application. This audio data output function may not be performed according to a setting or a user input.

The display 160 may include, for example, a liquid crystal display (LCD), a light-emitting diode (LED) display, an organic light-emitting diode (OLED) display, a microelectromechanical systems (MEMS) display, or an electronic paper display. The display 160 may present various content (e.g., a text, an image, a video, an icon, a symbol, or the like) to the user. The display 160 may include a touch screen, and may receive a touch, gesture, proximity or hovering input from an electronic pen or a part of a body of the user.

The display 160 may output at least one screen associated with an exercise function of the electronic device 100. According to an embodiment of the present disclosure, the display 160 may output at least one of map information, section information, synthetic information, or analysis information associated with the exercise function. The map information may present information within a certain range with respect to a current location of the electronic device 100 which is executing the exercise function. The map information may be magnified or reduced according to an input event. In the case where the map information is magnified, the display 160 may display more detailed local information with respect to a certain position. In the case where the map information is reduced, the display 160 may display local information which is relatively less detailed with respect to a certain position. While the map information is displayed, the display 160 may output at least one of the first object, the second object, the third object, or the fourth object based on exercise function-related sensor information obtained as the exercise function is performed.

The communication interface 170 may set communications between the electronic device 100 and an external device (e.g., the external electronic device 104 or the server 106). For example, the communication interface 170 may be connected to the network 162 via wireless communications so as to communicate with the external device (e.g., the external electronic device 104 or the server 106).

The wireless communications may employ at least one of cellular communication protocols such as long-term evolution (LTE), LTE-advance (LTE-A), code division multiple access (CDMA), wideband CDMA (WCDMA), universal mobile telecommunications system (UMTS), wireless broadband (WiBro), or global system for mobile communications (GSM). Furthermore, the wireless communications may include, for example, short-range communications. The short-range communications may include at least one of wireless fidelity (Wi-Fi), Bluetooth, near field communication (NFC), magnetic stripe transmission (MST), global navigation satellite system (GNSS), or the like. According to an embodiment of the present disclosure, the communication interface 170 may receive sensor information collected by the first and second sensors arranged in the external electronic device 104. Here, the communication interface 170 may receive the sensor information based on at least one of short-range communications or long-distance communications according to the type of a communication module provided to the communication interface 170.

The GNSS may include, for example, at least one of global positioning system (GPS), global orbiting navigation satellite system (GLONASS), BeiDou navigation satellite system (hereinafter referred to as "BeiDou"), Galileo, or European global satellite-based navigation system. Hereinafter, the term "GPS" and the term "GNSS" may be interchangeably used. The GNSS may collect and provide location information of the electronic device 100 (or the external electronic device 104).

A wired communication interface may include at least one of universal serial bus (USB), high definition multimedia interface (HDMI), recommended standard 232 (RS-232), plain old telephone service (POTS), or the like.

The exercise processing module 180 may perform various signal processing and data processing associated with the exercise function. In relation to this operation, the exercise processing module 180 may be provided so as to include at least one processor 120 or may operate as a part of the processor 120 to handle the exercise function. According to an embodiment of the present disclosure, the exercise processing module 180 may be provided in the form of software and may be uploaded to a processor so as to handle the exercise function. Alternatively, the exercise processing module 180 may be provided as individual hardware in relation to handling of the exercise function, and may perform data processing associated with the exercise function. As described above, the exercise processing module 180 may be provided as at least one of a software type or a hardware type.

Figure 2:
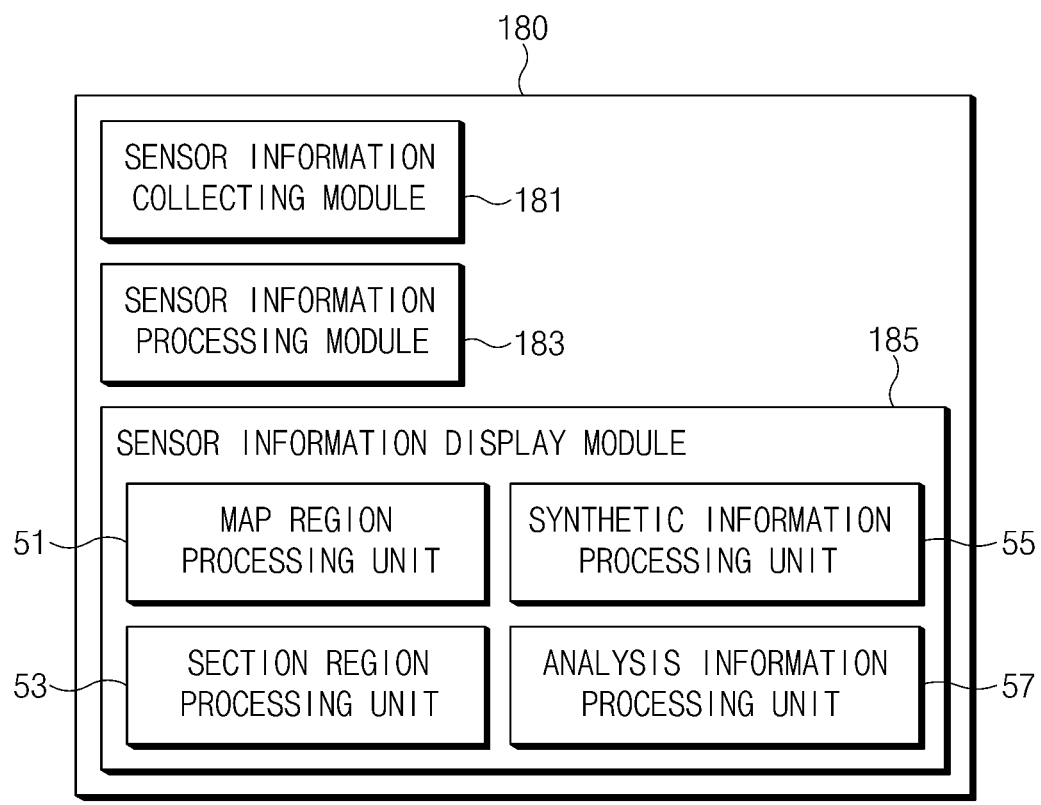
FIG. 2 is a diagram illustrating an example of an exercise processing module according to an embodiment of the present disclosure.

FIG. 2 is a diagram illustrating an example of an exercise processing module according to an embodiment of the present disclosure.

Referring now to FIG. 2, the exercise processing module 180 according to an embodiment of the present disclosure may include a sensor information collecting module 181, a sensor information processing module 183, and a sensor information display module 185.

The sensor information collecting module 181 may control enablement of the first and second sensors 191 and 192 and collection of sensor information. According to an embodiment of the present disclosure, if an exercise function execution request is made, the sensor information collecting module 181 may perform control so that the first and second sensors 191 and 192 are enabled. Furthermore, the sensor information collecting module 181 may collect sensor information of the enabled first and second sensors 191 and 192. In the case where the sensor information collecting module 181 is unable to collect the sensor information associated with the first sensor 191, the sensor information collecting module 181 may record information on a time (or section) at which the first sensor information is not collected. For example, the sensor information collecting module 181 may record information on a time at which GPS information is not received since the electronic device 100 is located in a building or a valley or between buildings. Furthermore, in the case where the sensor information collecting module 181 is unable to collect the sensor information associated with the second sensor 192, the sensor information collecting module 181 may record information on a time at which the second sensor information is not collected. For example, the sensor information collecting module 181 may record information on a time at which pedometer information (second information) is not received since the user moves not by walking or running (e.g., moves using a moving walk, a bicycle, a vehicle, or the like). The sensor information collecting module 181 may provide collected portions of sensor information to the sensor information processing module 183.

According to the various embodiments of the present disclosure, in the case where the sensor information is not collected, the sensor information collecting module 181 may perform control so that an alarm corresponding to this situation is output. For example, if at least one of the first sensor information (e.g., sensor information received in relation to the first sensor 191) or the second sensor information (e.g., sensor information received in relation to the second sensor 192) is not received, the sensor information processing module 183 may output guide information (e.g., at least one of visual information, audio information, vibration pattern information, lamp color information, or lamp flickering pattern information) notifying that corresponding sensor information is not received.

The sensor information processing module 183 may analyze at least a portion of sensor information received from the sensor information collecting module 181. For example, the sensor information processing module 183 may accumulate and store the first sensor information (e.g., GPS information). The sensor information processing module 183 may transfer, to the sensor information display module 185, connection information (e.g., a moving direction and a traveled distance) of the accumulated and stored portions of first sensor information.

The sensor information processing module 183 may calculate a moving speed and a distance traveled based on the first sensor information and the second sensor information received. For example, the sensor information processing module 183 may calculate a moving speed and an at least one of a plurality of sensors detecting movement of the electronic device, and the distance traveled of the electronic device 100 based on GPS information. Furthermore, the sensor information processing module 183 may calculate the moving speed based on the GPS information and pedometer information. According to an embodiment of the present disclosure, the sensor information processing module 183 may estimate the distance traveled or the moving speed of the electronic device 100 based on the pedometer information, and may compensate for a variation of portions of GPS information which is equal to or lager than or is less than a specified reference value.

According to an embodiment of the present disclosure, the sensor information processing module 183 may compare previously measured GPS information with currently measured GPS information. In the case where a location difference exceeds a specified value as a result of comparison, the sensor information processing module 183 may correct a movement position of the current GPS information based on the pedometer information. Furthermore, in the case where the pedometer information is equal to or larger than a certain value while the difference between the previous GPS information and the current GPS information does not exceed the specified value, the sensor information processing module 183 may correct the distance traveled and the moving speed of the electronic device 100 based on the pedometer information so that the distance traveled and the moving speed are larger than values calculated using the GPS information.

According to various embodiments of the present disclosure, if the first sensor information is not received, the sensor information processing module 183 may calculate the distance traveled and the moving speed based on the second sensor information alone. Likewise, if the second sensor information is not received, the sensor information processing module 183 may calculate the distance traveled and the moving speed based on the first sensor information alone. The sensor information processing module 183 may transfer, to the sensor information display module 185, information on the traveled distance, moving speed, and movement position. Furthermore, the sensor information processing module 183 may transfer, to the sensor information display module 185, information on sections in which the sensor information is not received.

The sensor information processing module 183 may determine whether the reference unit point (e.g., a unit position such as 500 m, 1 km, or the like) is passed based on the first sensor information and the second sensor information. In a state in which the electronic device 100 has passed the reference unit point, the sensor information processing module 183 may transfer, to the sensor information display module 185, location information on a specified distance-traveled position. The sensor information processing module 183 may divide received portions of sensor information by a reference unit distance, and may calculate a movement section in which an average moving speed of divided sections is highest among divided sections. Here, in the case where an exercise is ended between a space between a previous reference unit point and a next reference unit point, the sensor information processing module 183 may treat the space between the previous reference unit point and the next reference unit point as one section. The sensor information processing module 183 may transfer, to the sensor information display module 185, information on the movement section in which the average moving speed is highest (e.g., start position and end position information).

In the case where the section in which the first sensor information is not received overlaps with the movement section in which the average moving speed is highest, the sensor information processing module 183 may perform section adjustment according to a specified policy. For example, the sensor information processing module 183 may transfer, to the sensor information display module 185, location information of divided sections and highest-speed movement section information calculated according to the divided sections. Furthermore, in the case where the section in which the first sensor information is not received overlaps with an exercise end position, the sensor information processing module 183 may transfer, to the sensor information display module 185, information on the exercise end position and information on the section in which the sensor information is not received.

The sensor information display module 185 may output guide information associated with operation of the exercise function. According to an embodiment of the present disclosure, the sensor information display module 185, in relation to the operation of the exercise function, may perform visual information output control, audio information output control, control of output of a vibration with a specified pattern, control of a lamp emitting light of specified color, and control of a lamp flickering with a specified pattern. In relation to this operation, according to an embodiment of the present disclosure, the sensor information display module 185 may include a map region processing unit 51, a section region processing unit 53, a synthetic information processing unit 55, an analysis information processing unit 57.

The map region processing unit 51 may output map information. If the exercise function is executed, the sensor information display module 185 may receive, from the sensor information processing module 183, information on a certain region defined based on location information received by the first sensor 191. The map region processing unit 51 may output, to the display 160, map information with a specified size including a received certain region. The map region processing unit 51 may magnify or reduce an output map according to a user input. The map region processing unit 51 may output a route object corresponding to a distance traveled based on the first sensor information received from the sensor information processing module 183. The route information may be displayed on the map information. The route object may include at least one line connecting an exercise start position to an exercise end position.

The section region processing unit 53 may output the first object to the reference unit point provided by the sensor information processing module 183. For example, the section region processing unit 53 may output the first object to the reference unit point calculated based on the first sensor information and the second sensor information. According to an embodiment of the present disclosure, in the case where the reference unit point is provided in a plurality, the section region processing unit 53 may output the first objects (e.g., images or texts with different orders) differentiated for each reference unit point. The first object, for example, may be output to the map information.

In the case where there is no first sensor information for the reference unit point, the section region processing unit 53 may display a route object section including the corresponding reference unit point with the specified second object. For example, the section region processing unit 53 may output the route object section so that the route object section differs in at least one of line width or color from another section, thereby indicating that the first sensor information does not exist in the route object section. In the case where the first sensor information does not exist, the section region processing unit 53 may skip outputting the first object. The second object may be output to the map information (or route object).

If exercise end position information is received, the section region processing unit 53 may output the third object to the exercise end position. The third object may have a different shape (e.g., an image or a text, for example, a flag indicating an end of an exercise) from that of the first object. The section region processing unit 53 may display a section in which the first sensor information is not received or a section in which the second sensor information is not received differently from another section. For example, the section region processing unit 53 may display the section in which the first sensor information is not received in a first form, may display the section in which the second sensor information is not received in a second form, and may display a section in which both the first sensor information and the second sensor information are received in a third form.

The third object or the above-mentioned sections may be displayed on the route object (or a location, at least a part of which overlaps with the route object or which is adjacent to the route object within a specified distance). The section region processing unit 53 according to various embodiments of the present disclosure may differentially output, to a separate region, information on a moving speed for each section. Here, the section region processing unit 53 may divide an entire section by a reference unit based on the second sensor information, and may output information on a moving speed, etc. for divided sections.

The synthetic information processing unit 55 may output total exercise amount information provided by the sensor information processing module 183. For example, the synthetic information processing unit 55 may output information on a total distance from the exercise start position to the exercise end position and exercise time information for the total distance. According to various embodiments of the present disclosure, the synthetic information processing unit 55 may output exercise target information, information indicating whether an exercise target is achieved, information on comparison between a performed exercise amount and a specified reference exercise amount, or the like.

The analysis information processing unit 57 may output exercise analysis information. For example, the analysis information processing unit 57 may output information indicating whether an exercise has been done correctly or wrongly with respect to an exercise distance and an exercise speed based on an exercise reference value or a specified policy. Alternatively, the analysis information processing unit 57 may output information indicating an amount of exercise that should be done for a certain period based on an accumulated exercise amount or indicating an amount of exercise that has been done until a present time from a specified start position and an amount of exercise that should be done thereafter.

According to various embodiments of the present disclosure described above, an electronic device according to an embodiment of the present disclosure may include a non-transitory memory configured to store at least one instruction configured to output information in response to execution of an exercise function, and a processor connected to the memory, wherein the instruction executed by the processor may be configured to calculate a distance traveled based on a portion of sensor information received from a plurality of sensors for collecting sensing information according to a movement state, divide the calculated distance traveled by a specified reference unit, and output a specified object to a screen region including at least one reference unit point. In this operation, the electronic device may convert collected sensing information into information displayed on a screen and may output, based on the converted information, a mark or a specified object corresponding to the reference unit point, a specified object corresponding to a position corresponding to GPS coordinate information, or an object corresponding to a route or a position corresponding to distance traveled information, while outputting at least one object to the screen.

According to various embodiments of the present disclosure, the instruction executed will configure the processor to enable a GPS sensor and a pedometer sensor in response to execution of the exercise function.

According to various embodiments of the present disclosure, the instruction executed will configure the processor to output a route object corresponding to a total distance traveled based on GPS information among the portions of sensor information.

According to various embodiments of the present disclosure, the instruction executed will configure the processor to output, to the screen, a mark indicating the reference unit point.

According to various embodiments of the present disclosure, the instruction executed will configure the processor to output an object having order information to at least one screen portion corresponding to at least one reference unit point.

According to various embodiments of the present disclosure, the instruction executed by the processor may be configured to display a certain screen region corresponding to the reference unit point differently from a periphery of the certain screen region in the case where a portion of the sensor information corresponding to the reference unit point does not exist.

According to various embodiments of the present disclosure, the instruction executed will configure the processor to display the certain screen region corresponding to the reference unit point so that the certain screen region differs in at least one of line number, width, or color from the periphery of the certain screen region.

According to various embodiments of the present disclosure, the instruction executed will configure the processor to output an object corresponding to the reference unit point to a screen portion corresponding to a sensor information location collected immediately before the reference unit point in the case where the sensor information of the reference unit point and exercise end sensor information are equal in location.

According to various embodiments of the present disclosure, the instruction executed will configure the processor to calculate a moving speed based on the portion of sensor information, and perform screen display for a section with a highest moving speed, among sections divided for each reference unit point, so that the screen display differs from that for adjacent sections.

According to various embodiments of the present disclosure, the instruction executed will configure the processor to perform screen display for the position at which the portion of the sensor information does not exist so that the screen display differs from that for another section.

According to various embodiments of the present disclosure, the instruction executed will configure the processor to output guide information notifying a sensor information unreceived state if at least a portion of the sensor information is not received.

According to various embodiments of the present disclosure, the instruction executed will configure the processor to obtain time information of distance traveled information relatively closer to the reference unit point or corresponding to the reference unit point or time information of specified traveled distance information close to the reference unit point based on complex (different types of) pieces of sensor information, and select a screen portion corresponding to GPS coordinate information corresponding to the time information or GPS coordinate information of a time relatively close to the time information as a position to which the object is to be output.

Figure 3:
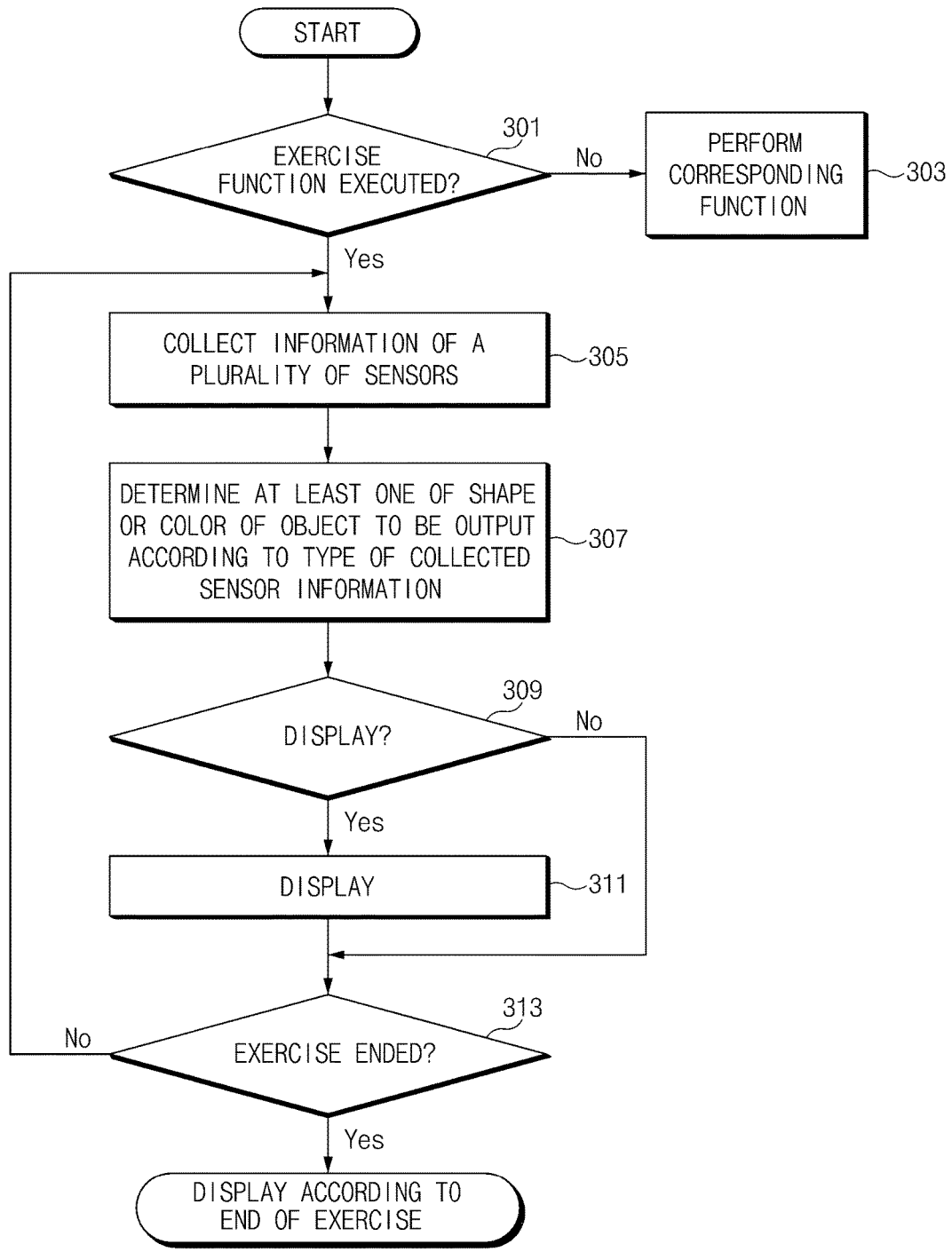
FIG. 3 is a diagram illustrating an electronic device operating method associated with an exercise function according to an embodiment of the present disclosure.

FIG. 3 is a diagram illustrating an electronic device operating method associated with an exercise function according to an embodiment of the present disclosure.

Referring to FIG. 3, in operation 301, the electronic device 100 may determine whether an event associated with execution of the exercise function occurs. The execution of the exercise function may be execution of a function associated with collection and analysis of sensor information according to an exercise. If the event associated with the execution of the exercise function does not occur, the electronic device 100 may perform a function according to the type of an event that has occurred or a corresponding function according to a specified scheduling event in operation 303. For example, the electronic device 100 may provide a music playback function, a video playback function, a web surfing function, or the like according to the type of the event that has occurred. According to various embodiments of the present disclosure, the electronic device 100 may output accumulated exercise amount information (e.g., pieces of exercise performance information performed during a specified period) according to an event type. An exercise amount information view function may be a function independently performed from an exercise function for collecting information according to performance of an exercise. Alternatively, the exercise amount information view function may be a function performed in response to selection of an information view function after an exercise application is executed.

If the event associated with the execution of the exercise function occurs, the electronic device 100 may collect information of a plurality of sensors in operation 305. For example, the electronic device 100 may enable the plurality of sensors configured to be enabled in relation to the execution of the exercise function. According to an embodiment of the present disclosure, the electronic device 100 may enable at least one sensor (e.g., the first sensor 191 and the second sensor 192) capable of detecting a movement or motion due to an exercise, and may collect sensor information based on the sensor. According to various embodiments of the present disclosure, in the case where a sensor associated with the execution of the exercise function is disposed in another external electronic device, the electronic device 100 may establish a communication channel to the external electronic device. The electronic device 100 may collect sensor information by requesting the external electronic device 104 to enable a plurality of sensors and transmit sensor information collected by the plurality of enabled sensors.

In operation 307, the electronic device 100 may determine at least one of the number, shape, or color of objects to be output according to the type of collected sensor information. According to an embodiment of the present disclosure, if a portion of a plurality sensor information is collected, the electronic device 100 may determine to output an object corresponding to a specified shape or color according to the type of collected sensor information. Furthermore, if all of the portions of sensor information are collected, the electronic device 100 may determine to output an object corresponding to a specified shape or color according to at least one of a distance traveled or a moving speed analyzed based on the portions of sensor information. For example, with respect to a section in which the first sensor information (e.g., GPS information) is not received but the second sensor information (e.g., pedometer information) is collected, the electronic device 100 may determine to output a first object (e.g., a free curve having a first width and a first color). With respect to a section in which the first sensor information (e.g., GPS information) is received but the second sensor information (e.g., pedometer information) is not collected, the electronic device 100 may determine to output a second object (e.g., a free curve having a second width and a second color).

In operation 309, the electronic device 100 may determine whether to display a determined object. For example, the electronic device 100 may determine whether object information is requested to be displayed. According to an embodiment of the present disclosure, the electronic device 100 may determine whether exercise performance information (e.g., a traveled distance, a moving speed, a moving direction, location information, or the like) is requested to be output in real time. Alternatively, in the case where the exercise performance information is configured to be displayed at a time of an end of an exercise, the electronic device 100 may determine whether an event indicating the end of the exercise is received. Alternatively, the electronic device 100 may determine whether an event (e.g., occurrence of a user input or reaching a specified distance) for requesting display of the exercise performance information occurs.

If a display request-related event occurs, the electronic device 100 may output a determined object to the display 160 in operation 311. According to an embodiment of the present disclosure, the electronic device 100 may output the determined object to map information. Alternatively, the electronic device 100 may output section information including the determined object without outputting the map information. If the display request-related event does not occur, the electronic device 100 may skip outputting an object.

In operation 313, the electronic device 100 may determine whether an event associated with the end of the exercise occurs. For example, the electronic device 100 may determine whether a user input event indicating the end of the exercise is received. Alternatively, the electronic device 100 may determine whether an event indicating achievement of a specified exercise target occurs.

If the event associated with the end of the exercise does not occur, the process may return to operation 305 so that the electronic device 100 may re-perform operation 305 and the following operations. Alternatively, the process may return to operation 311 so that the electronic device 100 may maintain an object display state. If the event associated with the end of the exercise occurs, the electronic device 100 may perform display according to the end of the exercise. For example, the electronic device 100 may output, to the display 160, at least one of map information, section information, or synthetic information according to a specified setting. According to an embodiment of the present disclosure, the electronic device 100 may output a specified object (e.g., an end mark, for example, a flag) to the map information according to an end position at which the exercise end event has occurred. Furthermore, if the exercise end event occurs, the electronic device 100 may perform exercise amount analysis and may output an analysis result. When the exercise end event occurs, the electronic device 100 may store the exercise performance information in a specified region (e.g., the exercise database 131) of the memory 130.

Figure 4:
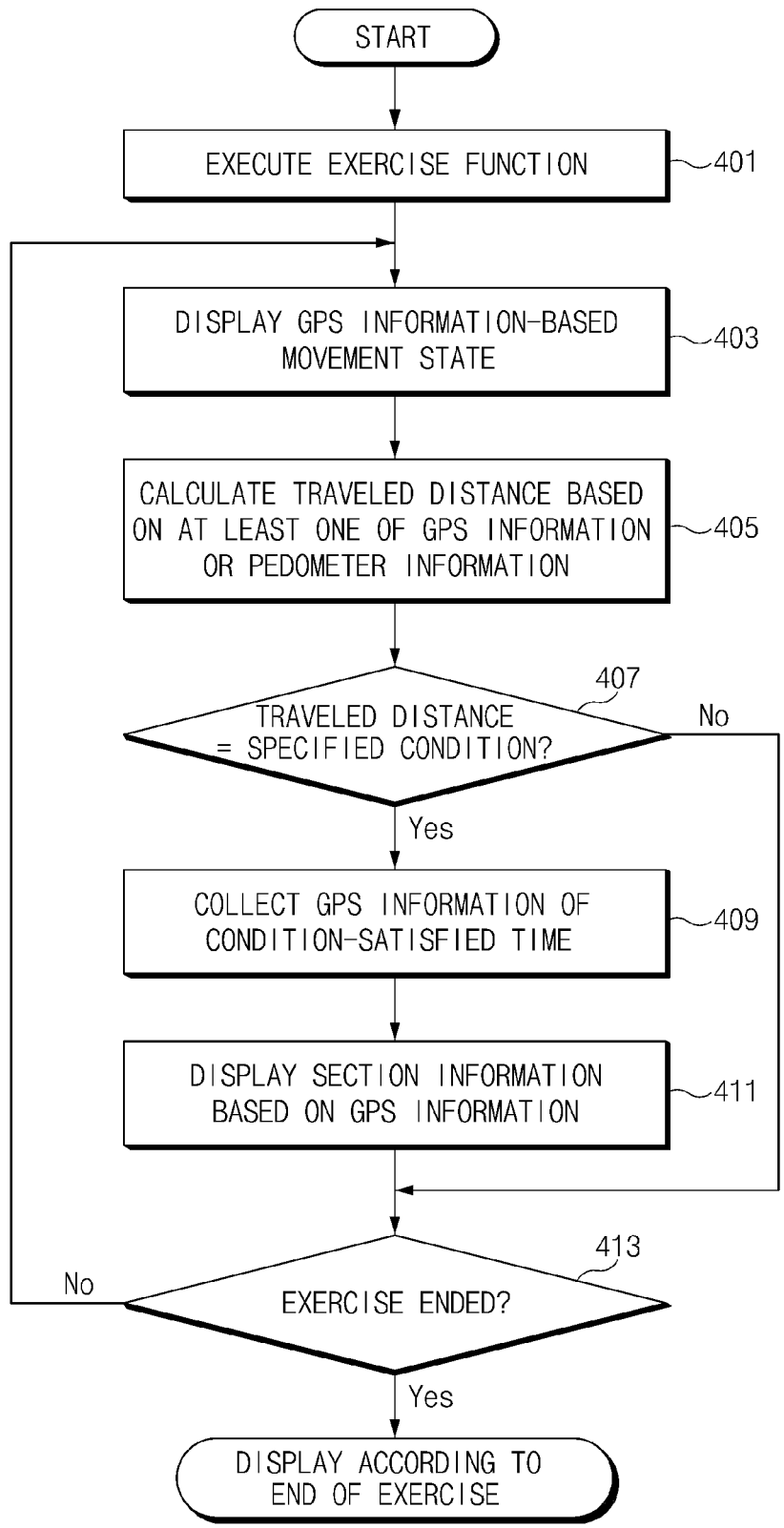
FIG. 4 is a diagram illustrating an electronic device operating method associated with an exercise function supporting display of section information according to an embodiment of the present disclosure.

FIG. 4 is a diagram illustrating an electronic device operating method associated with an exercise function supporting display of section information according to an embodiment of the present disclosure.

Referring to FIG. 4, in operation 401, the electronic device 100 may execute the exercise function in response to occurrence of a specified input event (or arrival of a specified schedule). For example, the electronic device 100 may activate an exercise application. The electronic device 100 may output a virtual key button for selecting enablement of at least one sensor (e.g., a GPS sensor and a pedometer sensor). According to an embodiment of the present disclosure, the electronic device 100 may output a virtual key button configured to simultaneously enable a GPS sensor and a pedometer sensor. As the exercise function is executed, the electronic device 100 may enable the GPS sensor and the pedometer sensor. While the exercise function is executed, the electronic device 100 may collect GPS information and pedometer information. According to an embodiment of the present disclosure, the electronic device 100 may store time information and coordinate information at which the GPS information is collected. Furthermore, the electronic device 100 may store speed information and distance information calculated based on the GPS information and the pedometer information and time information at which the speed information and distance information are collected. According to an embodiment of the present disclosure, the electronic device 100 may store each coordinate information or speed and distance information on a per-specified time basis (e.g., second or minute basis).

In operation 403, the electronic device 100 may display a GPS information-based movement state. For example, if there is a setting for requesting real-time display of the exercise performance information or a user input for requesting display of the exercise performance information, the electronic device 100 may display the GPS information-based movement state. Alternatively, the electronic device 100 may recognize occurrence of an event indicating an end of an exercise as occurrence of an event for displaying the exercise performance information, and may display the exercise performance information.

In operation 405, the electronic device 100 may calculate a distance traveled based on at least one of the GPS information or the pedometer information. For example, the electronic device 100 may calculate the distance traveled based on the GPS information and may correct a GPS result with the pedometer information in a section in which both the GPS information and the pedometer information exist. According to various embodiments of the present disclosure, in the case where only the GPS information exists, the electronic device 100 may calculate at least one of the distance traveled or moving speed based on the GPS information. In the case where only the pedometer information exists, the electronic device 100 may calculate at least one of the distance traveled or moving speed based on the pedometer information alone.

In operation 407, the electronic device 100 may determine whether the calculated distance traveled satisfies a specified condition. For example, the electronic device 100 may determine whether the calculated distance traveled reaches a specified reference unit point (e.g., 1 km, etc.). In the case where the calculated distance traveled satisfies the specified condition, the electronic device 100 may collect the GPS information of a time at which the condition is satisfied in operation 409. For example, in the case where the distance traveled calculated based on the GPS information and the pedometer information reaches the reference unit point, the electronic device 100 may check a GPS information collection time matched to a reached time at which the traveled distance exceeds the reference unit point. The electronic device 100 may determine coordinate information corresponding to the checked GPS information collection time as reference unit point information satisfying the specified condition.

According to various embodiments of the present disclosure, in the case where the time reached does not match the GPS information collection time, the electronic device 100 may select information based on an approximate value for a specified position (e.g., the reference unit point). For example, the electronic device 100 may obtain information associated with reaching the reference unit point 1 km based on complex sensor information (e.g., GPS information and pedometer information) accumulated as an exercise is performed. According to an embodiment of the present disclosure, the electronic device 100 may obtain information in which movement time information and distance traveled information calculated based on the GPS information and the pedometer information are 9.9 km at 10 minutes and 10 seconds and 10.3 km at 10 minutes and 10 seconds. In this case, the electronic device 100 may select the movement time 10 minutes and 10 seconds, the distance traveled at which relatively approximates to the reference unit point 1 km. If there exist the movement time information and the distance traveled information corresponding to the reaching the reference unit point 1 km, the electronic device 100 may select the movement time information.

If the information corresponding to 10 minutes and 10 seconds associated with the reference unit point is obtained, the electronic device 100 may obtain GPS coordinate information corresponding to the information. In relation to this operation, the electronic device 100 may accumulate and store the GPS coordinate information and time information of each piece of coordinate information. According to an embodiment of the present disclosure, if there exist 10 minutes and 7 seconds and 10 minutes and 11 seconds in the accumulated time information, the electronic device 100 may select the GPS coordinate information of 10 minutes and 11 seconds which relatively approximate to 10 minutes and 10 seconds. Accordingly, the electronic device 100 may output an object indicating the reference unit point based on the GPS coordinate information corresponding to 10 minutes and 11 seconds.

In the case where there is no GPS coordinate information within a certain range with respect to the reference unit point, for example, in the case where there is no GPS coordinate information within a distance (e.g., a specific distance of at least 500 m) specified with respect to a reference unit distance 1 km, the electronic device 100 may output a certain region including the reference unit point as a specified object (e.g., a line having a specified width and color).

In operation 411, the electronic device 100 may display GPS information-based section information. For example, the electronic device 100 may output an object (e.g., a specified image or number information indicating a reference unit point) to a determined reference unit point while a movement state is displayed (e.g., a route object is output) based on the GPS information. The electronic device 100 may output, to the map information, the movement state and a reference unit point indicating object. According to various embodiments of the present disclosure, the electronic device 100 may arrange section information based on reference unit points. The section information may include moving speed information (e.g., an average section movement speed) of each section.

In operation 413, the electronic device 100 may determine whether an event associated with an end of an exercise occurs. If an exercise end event occurs, the electronic device 100 may stop collecting sensor information associated with exercise performance. The electronic device 100 may perform a display operation (e.g., displaying a screen or an object notifying the end of the exercise) according to the end of the exercise. If the exercise is not ended, the process may return to operation 403 so that the electronic device 100 may display information according to a setting or an event.

Figure 5:
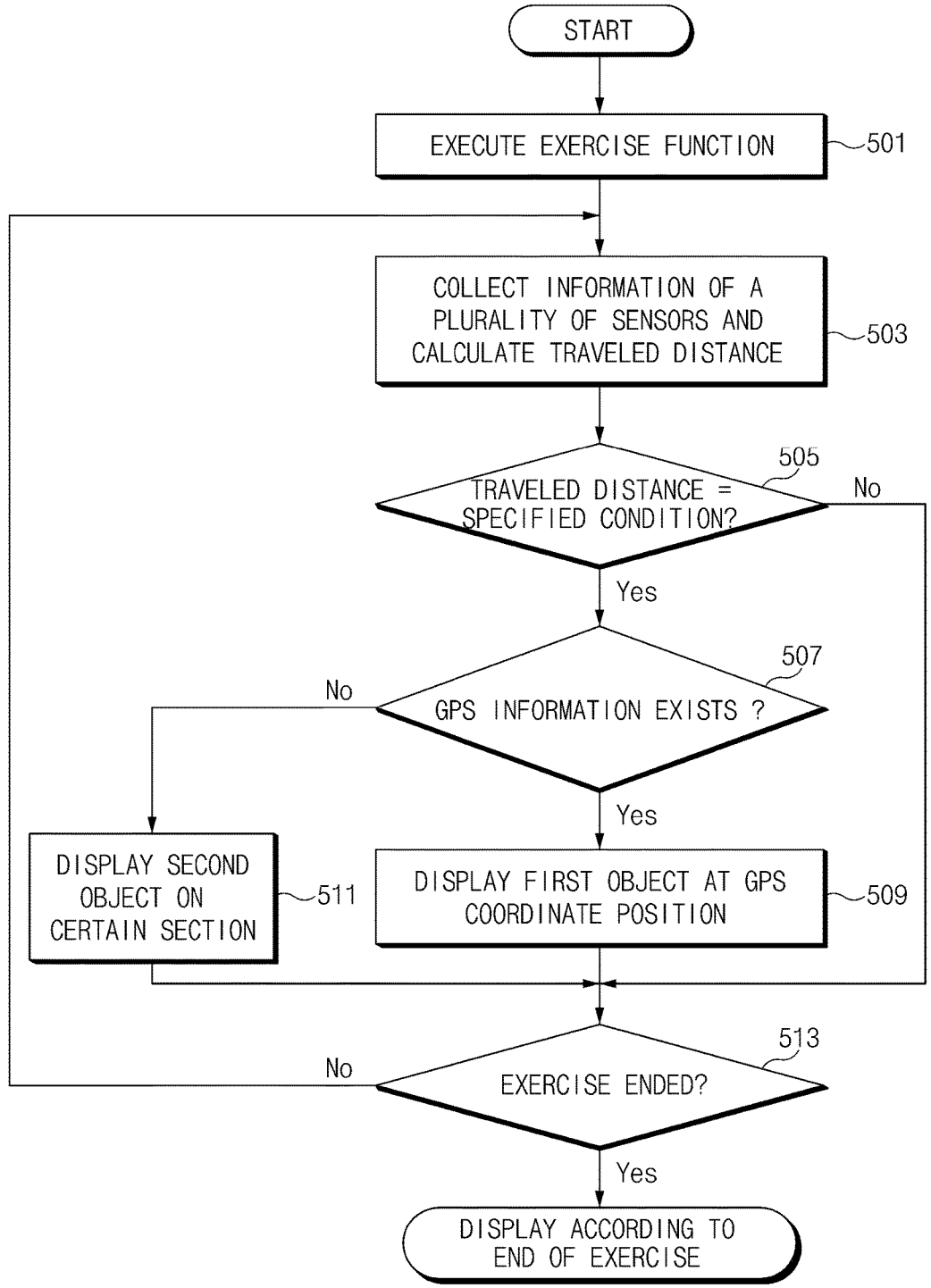
FIG. 5 is a diagram illustrating an electronic device operating method associated with an exercise function supporting display of various objects according to an embodiment of the present disclosure.

FIG. 5 is a diagram illustrating an electronic device operating method associated with an exercise function supporting display of various objects according to an embodiment of the present disclosure.

Referring to FIG. 5, in operation 501, the electronic device 100 may execute the exercise function in response to occurrence of a specified input event (or arrival of a specified schedule). As the exercise function is executed, the electronic device 100 may enable the GPS sensor and the pedometer sensor.

In operation 503, the electronic device 100 may perform collection of information of a plurality of sensors and calculation of a traveled distance. According to an embodiment of the present disclosure, while the exercise function is executed, the electronic device 100 may collect GPS information and pedometer information. In this operation, the electronic device 100 may store time information and coordinate information at which the GPS information is collected. Furthermore, the electronic device 100 may store moving speed information and distance traveled information calculated based on the GPS information and the pedometer information and time information at which the speed information and distance information are collected. According to an embodiment of the present disclosure, the electronic device 100 may store each coordinate information or speed and distance information on a per-specified time basis (e.g., second or minute basis). In the case where location information and distance traveled and speed information calculated from the GPS sensor information and speed and distance-corrected information calculated based on the GPS sensor and the pedometer sensor are supplied from individual engines respectively, a difference between an information collection time and an information transfer time may occur. Therefore, the electronic device 100 may store information with a specified reference time for each information. For example, the electronic device 100 may store, based on a time at which the GPS information is collected, distance traveled information and moving speed information calculated based on the GPS information and the pedometer information.

In relation to distance traveled calculation, the electronic device 100 may calculate a distance traveled and a moving speed based on a distance difference and a time difference between the GPS information collected at a certain time and the GPS information collected after elapse of a specified time thereafter. The electronic device 100 may perform distance and speed correction on the distance traveled and the moving speed calculated based on the GPS information, using the pedometer information.

In operation 505, the electronic device 100 may determine whether the calculated distance traveled satisfies a specified condition. For example, the electronic device 100 may determine whether the calculated distance traveled reaches a reference unit point (e.g., several meters or kilometers). In the case where the calculated distance traveled satisfies the specified condition, the electronic device 100 may determine whether the GPS information exists at a position at which the condition is satisfied in operation 507. For example, the electronic device 100 may obtain time information satisfying the distance traveled of the specified condition. The electronic device 100 may determine whether the GPS information corresponding to the obtained time information exits.

In the case where the GPS information exists, the electronic device 100 may display a first object at GPS coordinates in operation 509. Here, the first object may include at least one of an image or a text indicating reaching a reference unit point.

In the case where the GPS information does not exist, the electronic device 100 may display a second object on a certain section in operation 511. For example, the electronic device 100 may display the certain section including the reference unit point differently (e.g., differently in terms of at least one of color or width) from an adjacent section.

In operation 513, the electronic device 100 may determine whether an event associated with the end of the exercise occurs. If the event associated with the end of the exercise does not occur, the process may return to operation 503 so that the electronic device 100 may re-perform operation 503 and the following operations. If the event associated with the end of the exercise occurs, the electronic device 100 may perform display according to the end of the exercise. For example, the electronic device 100 may output a specified object (e.g., at least one of an image or a text indicating the end of the exercise) to an exercise end position. The electronic device 100 may output total exercise amount information, exercise analysis information, or the like. The electronic device 100 may output map information, section information, or the like. The electronic device 100 may stop displaying information if a specified time elapses after the above-mentioned information is displayed or according to a user input.

According to various embodiments of the present disclosure described above, a sensor information using method according to an embodiment of the present disclosure may include collecting at least a portion of sensor information according to a movement state using a plurality of sensors, calculating a distance traveled based on collected portions of sensor information, dividing the calculated distance traveled by a specified reference unit, and outputting a specified object to a screen region including at least one reference unit point.

According to various embodiments of the present disclosure, the collecting may include collecting at least one of GPS sensor information or pedometer sensor information according to execution of an exercise function.

According to various embodiments of the present disclosure, the method may further include outputting, to a screen, a route object corresponding to a total distance traveled based on GPS information among the portions of sensor information.

According to various embodiments of the present disclosure, the outputting may include outputting, to the screen, a mark indicating the reference unit point.

According to various embodiments of the present disclosure, the outputting may include outputting an object having order information to at least one screen portion corresponding to at least one reference unit point.

According to various embodiments of the present disclosure, the outputting may include displaying a certain screen region corresponding to the reference unit point differently from a periphery of the certain screen region in the case where a portion of the sensor information corresponding to the reference unit point does not exist.

According to various embodiments of the present disclosure, the displaying may include displaying the certain screen region corresponding to the reference unit point so that the certain screen region differs in at least one of line number, width, or color from the periphery of the certain screen region.

According to various embodiments of the present disclosure, the outputting may include outputting an object corresponding to the reference unit point to a screen portion corresponding to a sensor information location collected immediately before the reference unit point in the case where the sensor information of the reference unit point and exercise end sensor information are equal in location.

According to various embodiments of the present disclosure, the outputting may include calculating a moving speed based on the portions of sensor information and performing screen display for a section with a highest speed among sections divided for each reference unit point differently from screen display for peripheral sections.

According to various embodiments of the present disclosure, the outputting may include performing screen display for the position at which the portion of the f sensor information does not exist differently (i.e. is the same as) from the screen display for another section.

According to various embodiments of the present disclosure, the outputting may include obtaining time information of distance traveled information relatively closer to the reference unit point or corresponding to the reference unit point based on complex portions of sensor information, and selecting a screen portion corresponding to GPS coordinate information corresponding to the time information or GPS coordinate information of a time relatively close to the time information as a position to which the object is to be output.

Figure 6:
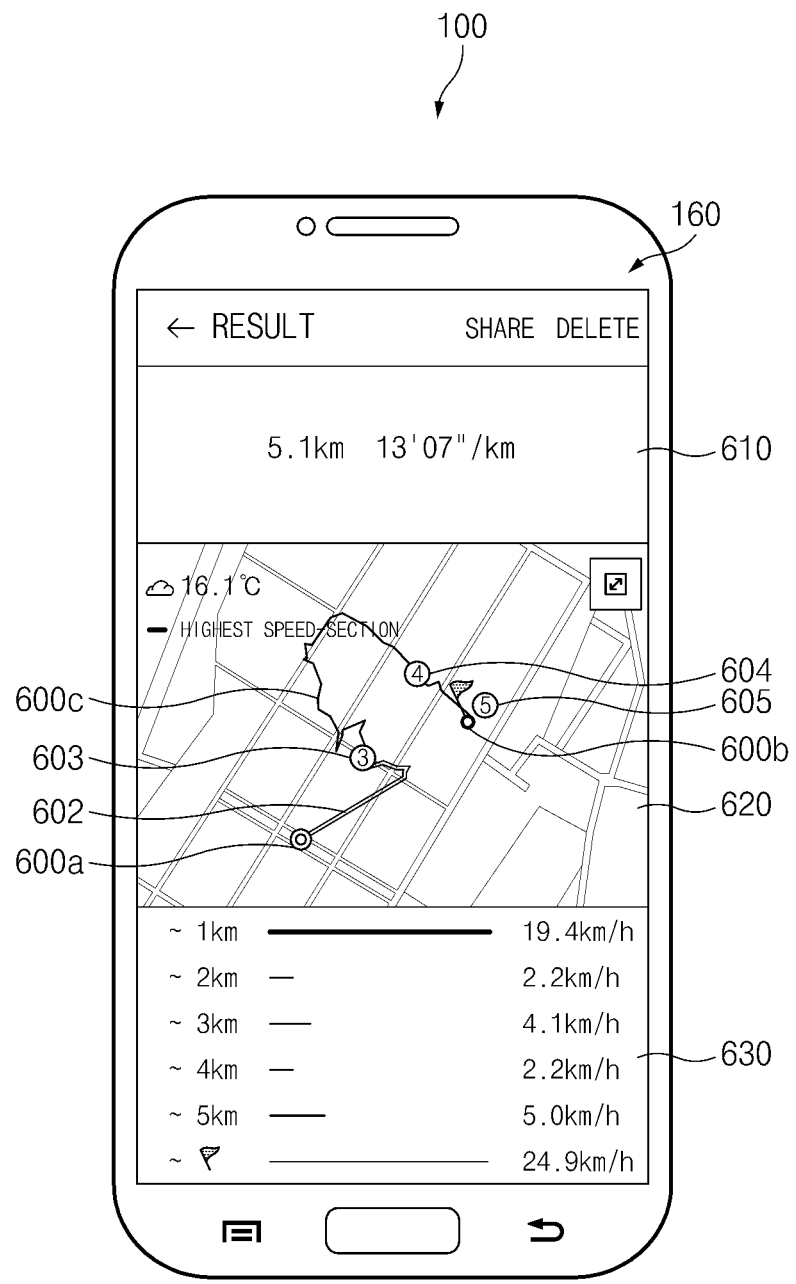
FIG. 6 is a diagram illustrating an exercise performance information display screen including a first sensor information unreceived section according to an embodiment of the present disclosure.

FIG. 6 is a diagram illustrating an exercise performance information display screen including a first sensor information unreceived section according to an embodiment of the present disclosure.

Referring now to FIG. 6, the display 160 of the electronic device 100 may output a screen including a synthetic information region 610, a map information region 620, and a section information region 630. According to various embodiments of the present disclosure, the electronic device 100 may further output, to the display 160, an analysis information region to which analysis information obtained by analyzing exercise performance information is output.

The synthetic information region 610 may include total exercise amount information collected according to performance of an exercise. For example, the synthetic information region 610 may include information on a total distance traveled and total performance time information corresponding to the total traveled distance. The synthetic information region 610 may be output to a certain portion (e.g., upper end) of the screen.

The map information region 620 may include map information. The map information region 620 may include a route object 600*c* output to the map information. The route object 600*c* may be an image corresponding to the total traveled distance. A start mark 600*a*, movement marks 603 to 605 corresponding to a unit distance, and an end mark 600*b* may be arranged on the route object 600*c*. The start mark 600*a* may correspond to a sensor information collection start position. For example, the start mark 600*a* may correspond to GPS information of the sensor information collection start position. The movement marks 603 to 605 may be displayed on specified reference unit points. For example, in the case where a reference unit point is 1 km and the total distance traveled is 5.1 km, the movement marks may be respectively displayed on five reference unit points. The movement marks may include order information according to an assigned order.

According to various embodiments of the present disclosure, the electronic device 100 may skip outputting the movement mark in response to the nonexistence of GPS information. For example, in the case where there is no GPS information for a first reference unit point (e.g., a position to which 1 km is traveled from a start position) and a second reference unit point (e.g., a position to which 2 km are traveled from a start position), the electronic device 100 may skip outputting movement marks corresponding to the foregoing positions. In the case where there exists GPS information corresponding to a third reference unit point, the electronic device 100 may display the third movement mark 603 after the start mark 600*a*. According to various embodiments of the present disclosure, the electronic device 100 may output a specified object 602 (e.g., a line which differs in color or width from a periphery thereof) instead of outputting first and second movement marks.

The end mark 600*b* may be output based on GPS coordinate information of a position at which an exercise end event occurs. In the case where an exercise end position is the same as a movement mark position, the electronic device 100 may adjust an output location of the movement mark position. For example, referring to FIG. 6, the electronic device 100 may output the fifth movement mark 605 to a 5 km position. In the case where the exercise end position is the same as the position to which the fifth movement mark 605 is output and a total exercise distance is 5.1 km, the electronic device 100 may output the end mark 600*b* to the position to which the fifth movement mark 605 is to be output. The fifth movement mark 605 may be output to a position moved by a specified distance (e.g., a position of GPS coordinate information obtained immediately before GPS coordinate information at which the fifth movement mark 605 is displayed is obtained).

The section information region 630 may include section information divided based on each reference unit point. For example, the section information region 630 may output moving speed information of a 0-1 km section, moving speed information of a 1-2 km section, moving speed information of a 2-3 km section, moving speed information of 3-4 km section, moving speed information of 4-5 km section, and moving speed information of a section between 5 km and exercise end position. The electronic device 100 may display a section with a highest moving speed (e.g., 0-1 km) differently from another section by comparing moving speed information with each other based on pedometer information even if GPS information does not exist. According to an embodiment of the present disclosure, the electronic device 100 may display an image corresponding to the section with the highest moving speed so that the image differs in at least one of size (or width) or color from another image.

Figure 7:
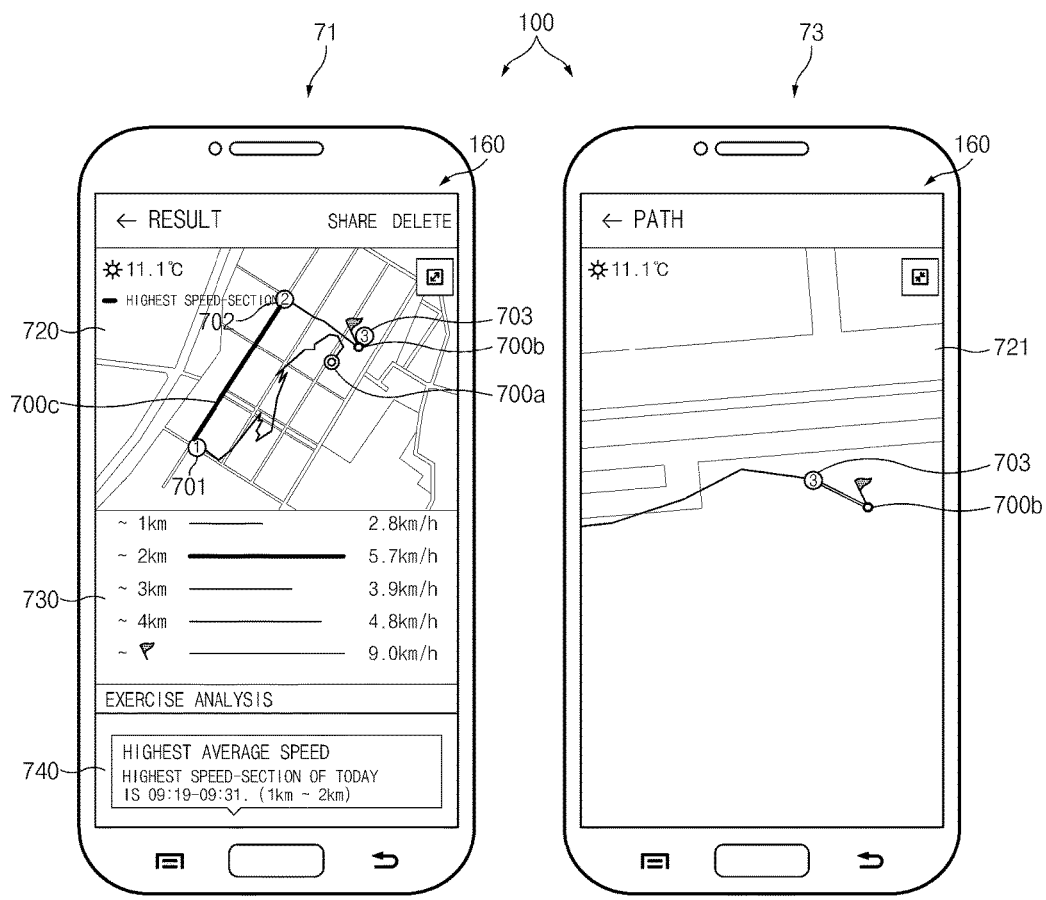
FIG. 7 is a diagram illustrating an exercise performance information display screen according to an end of an exercise in a first sensor information unreceived section according to an embodiment of the present disclosure.

FIG. 7 is a diagram illustrating an exercise performance information display screen according to an end of an exercise in a first sensor information unreceived section according to an embodiment of the present disclosure.

Referring to FIG. 7, the display 160 of the electronic device 100 may include a map information region 720, a section information region 730, and an analysis information region 740 as illustrated in a state 71.

The map information region 720 may include a route object 700*c*, a start mark 700*a*, an end mark 700*b*, and movement marks 701 to 703 displayed on map information determined according to a location of the electronic device 100. The route object 700*c* may be displayed based on GPS information among portions of information collected according to execution of an exercise function. The start mark 700*a* may be disposed at a start position of the route object 700*c*, and the end mark 700*b* may be disposed at an end position of the route object 700*c*. A display location of the start mark 700*a*, for example, may be determined based on initial GPS information obtained by the first sensor 191 enabled in response to an exercise function execution request. A display location of the end mark 700*b*, for example, may be determined based on GPS information lastly obtained by the first sensor 191 in response to an exercise function end request. The movement marks 701 to 703, for example, may include a first movement mark 701, a second movement mark 702, and a third movement mark 703 displayed on sections in which GPS information exists. The third movement mark 703 may be displayed on a region adjacent to the end mark 700*b*. A total distance traveled may be 4.22 km, and GPS information may exist until 3 km of the total distance traveled is reached but GPS information may not exist between the 3-km position and the exercise end position. Accordingly, the fourth movement mark may not be displayed.

The section information region 730 may divide the total distance traveled for each reference unit point and may display a moving speed for each reference unit point. During a process of selecting a moving speed of a highest speed-section, the electronic device 100 may select a moving speed at a reference unit point (e.g., 1 km). Alternatively, the electronic device 100 may exclude information of a section (e.g., the section between the 4-km position and the end position) lacking GPS information. Accordingly, the electronic device 100 may select the 1-2 km section as a highest speed-section. The section information region 730 may display a section (e.g., the 1-2 km section) corresponding to a moving speed equal to or higher than a specified value or a highest moving speed differently from another section. For example, the 1-2 km section may differ in at least one of line width or color from another section.

The analysis information region 740 may display information obtained by analyzing a result of performing an exercise. According to an embodiment of the present disclosure, the analysis information region 740 may provide, for example, information on a specific section with a highest average speed. The analysis information region 740 may also output information on an overall exercise state.

The display 160 of the electronic device may output a map information magnification region 721 as illustrated in a state 73. For example, if a specified event (e.g., an event for requesting magnification of an image) occurs on the map information region 720, the electronic device 100 may magnify the map information region 720 based on a position at which the event has occurred or a specified location.

The map information magnification region 721 may include, for example, a region in which the position at which the end mark 700b is disposed is magnified. In relation to this operation, if a specified event occurs on the position at which the end mark 700b is disposed, the electronic device 100 may magnify and display a certain region around the end mark 700b. The third movement mark 703 and the end mark 700b may be arranged on the map information magnification region 721, and a specified object may be displayed between the third movement mark 703 and the end mark 700b. The specified object may be an object replacing the fourth movement mark. According to an embodiment of the present disclosure, the specified object may be an object which differs in at least one of line number, line width, or line color from another section.

In the case where GPS coordinate information for a position at which an exercise end event occurs does not exist (e.g., in the case where the electronic device 100 is located in an area, such as the inside of a building, where the electronic device 100 is unable to receive GPS information at a time of an end of an exercise), the electronic device 100 may output the end mark 700b to a position at which GPS coordinate information exists. According to an embodiment of the present disclosure, the exercise may end at the 4.22 km position in a state in which GPS coordinate information exists at the 3-km position but the GPS coordinate information does not exist thereafter. In this case, the electronic device 100 may output the end mark 700b to the 3-km position. Alternatively, the electronic device 100 may output the third movement mark 703 to the 3-km position and may output the end mark 700b to a position spaced apart from the 3-km position by the specified object.

Figure 8:
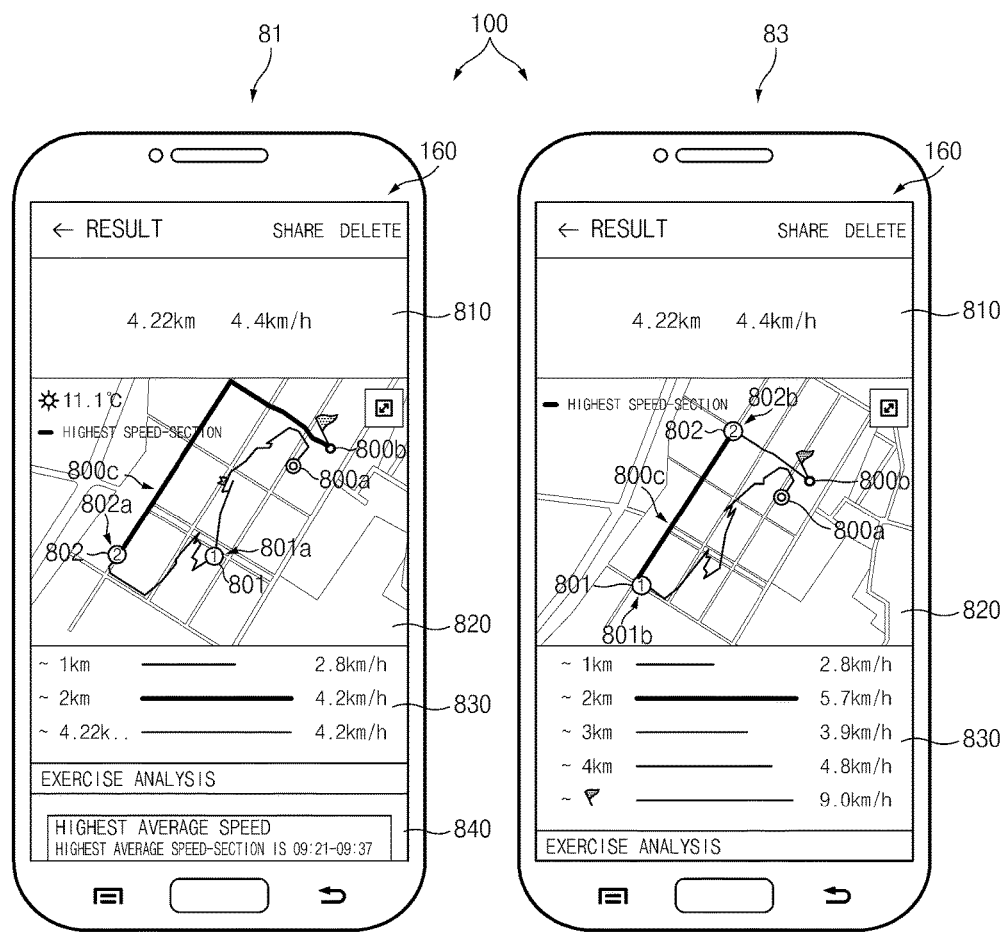
FIG. 8 is a diagram illustrating an exercise performance information display screen according to correction of first sensor information according to an embodiment of the present disclosure.

FIG. 8 is a diagram illustrating an exercise performance information display screen according to correction of first sensor information according to an embodiment of the present disclosure.

Referring now to FIG. 8, as illustrated in a state 81, the display 160 of the electronic device 100 may display a route object 800c on the display 160 using the first sensor information alone. Furthermore, the electronic device 100 may display a reference unit point (e.g., display a mark every time 1 km is traveled) using the first sensor information alone. In the case where movement marks are displays using the first sensor information alone, the electronic device 100 may output a first movement mark 801 to a first position 801a and may output a second movement mark 802 to a second position 802a. Furthermore, the electronic device 100 may output, to a third position 801b, an end mark 800b according to an end of an exercise.

According to various embodiments of the present disclosure, in the case where the first sensor information is corrected using second sensor information, the display 160 of the electronic device 100 may display the reference unit points as illustrated in a state 83. For example, the electronic device 100 may output the first movement mark 801 to the third position 801b and may output the second movement mark 802 to a fourth position 802b. As described above, the electronic device 100 may arrange the first movement mark 801 and the second movement mark 802 at the third position 801b and the fourth position 802b which are relatively close to actual traveled distance.

According to various embodiments of the present disclosure, the electronic device 100 may be in a state of having traveled 4.22 km. The electronic device 100 may be in a state of not having received at least a part of GPS information after travelling 2 km. Accordingly, the electronic device 100 may not have obtained GPS information for displaying a third movement mark and a fourth movement mark. In this case, the electronic device 100 may output a specified object (e.g., at least one of an image or a text configured to be displayed instead of movement marks) between the second movement mark 802 and the end mark 800b.

The electronic device 100 may further output synthetic information region 810, section information region 830, and analysis information region 840. The electronic device 100 may display information on some sections (e.g., 0-1 km section and 1-2 km section) on the section information region 830 displayed using the first sensor information alone. The electronic device 100 may display all sections (e.g., 0-1 km section, 1-2 km section, 2-3 km section, 3-4 km section, and section between 4 km position and end position) on the section information region 830 displayed using the first sensor information and the second sensor information.

Figure 9:
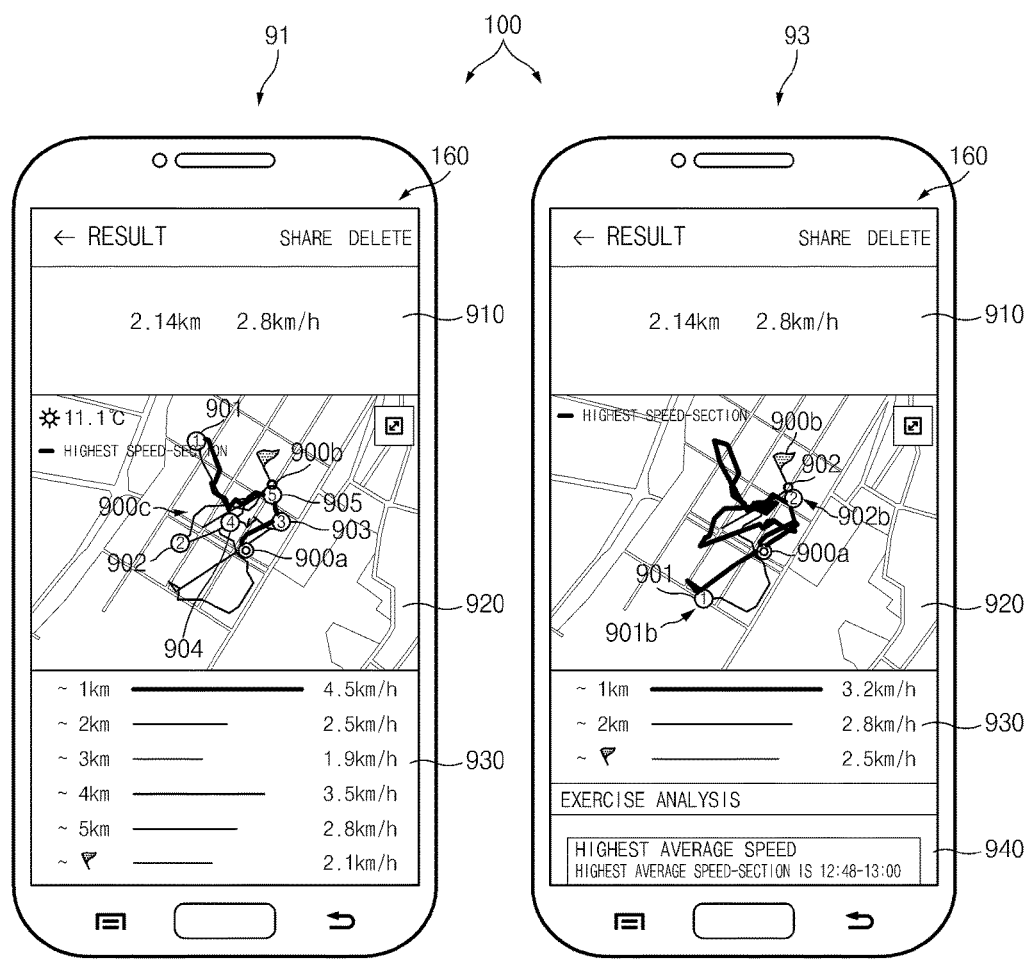
FIG. 9 is a diagram illustrating another example of an exercise performance information display screen according to correction of first sensor information according to an embodiment of the present disclosure.

FIG. 9 is a diagram illustrating another example of an exercise performance information display screen according to correction of first sensor information according to an embodiment of the present disclosure.

Referring to FIG. 9, as illustrated in a state 91, the display 160 of the electronic device 100 may output, to a map information region 920, a route object 900c according to the first sensor information. The electronic device 100 may calculate a reference unit point using the first sensor information alone, and may output a first movement mark 901, a second movement mark 902, a third movement mark 903, a fourth movement mark 904, and a fifth movement mark 905 according to a calculated unit distance. Furthermore, the electronic device 100 may output a start mark 900a according to a start of an exercise and an end mark 900b according to an end of the exercise. Information error may occur on the first sensor information, for example, GPS information due to an environment such as a periphery of a building or the inside thereof as described above.

According to various embodiments of the present disclosure, in the case where the electronic device 100 corrects the first sensor information using second sensor information (e.g., pedometer information), the display 160 may output a screen as illustrated in a state 93. For example, the electronic device 100 may output the first movement mark 901 to a first position 901b different from the position of the first movement mark 901 of the state 91, and may output the second movement mark 902 to a second position 902b different from the position of the second movement mark 902 of the state 91. Since the total distance traveled is 2.14 km, the electronic device 100 may display two movement marks to indicate reference unit points.

In the case where section information region 930 is displayed using the first sensor information alone, information on six sections may be displayed in the state 91. In the case where the section information region 930 is displayed based on the first sensor information and the second sensor information, information on three sections may be displayed in the state 93. In addition, the electronic device 100 may output an exercise analysis result to an analysis information region 940.

Figure 10:
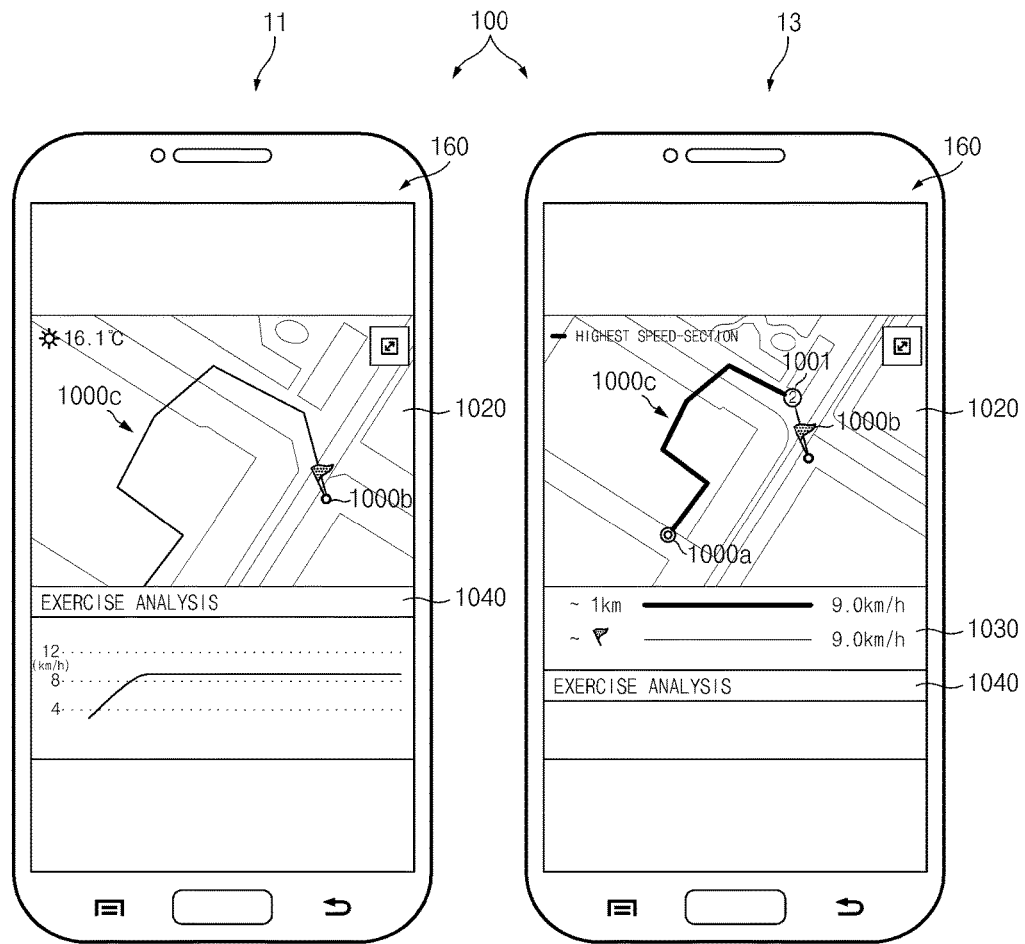
FIG. 10 is a diagram illustrating an example of an exercise performance information display screen according to error correction of first sensor information according to an embodiment of the present disclosure.

FIG. 10 is a diagram illustrating an example of an exercise performance information display screen according to error correction of first sensor information according to an embodiment of the present disclosure.

Referring to now FIG. 10, in the case where a distance traveled calculated based on first sensor information is less than a reference unit point (e.g., 1 km) even if the electronic device 100 has traveled at least 1 km, the display 160 of the electronic device 100 may output, to map information region 1020, a route object 1000c indicating that the reference unit point is not reached. Since the distance traveled calculated using the first sensor information alone does not reach the reference unit point (e.g., 1 km), the electronic device 100 may not display an additional movement mark. The electronic device 100 may output an end mark 1000b to an end position of the route object 1000c. In a section information region 1030, the electronic device 100 may display information on moving speeds of all sections (e.g., a section of a distance not reaching a reference unit point).

According to various embodiments of the present disclosure, in the case where a distance traveled is measured based on second sensor information in addition to the first sensor information, as illustrated in a state 13, the electronic device 100 may calculate a distance traveled equal to or larger than a reference unit point (e.g., 1 km) unlike calculation in a state 11. Accordingly, the display 160 of the electronic device 100 may output a first movement mark 1001 to the route object 1000c. Furthermore, the electronic device 100 may output the end mark 1000b to a position spaced apart from the first movement mark 1001 by a certain distance. As the reference unit point is calculated, the electronic device 100 may display, on the section information region 1030, moving speed information corresponding to a first section (e.g., 0-1 km). Furthermore, the electronic device 100 may display, on the section information region 1030, moving speed information corresponding to a section between the 1 km-position and the end position. In addition, the electronic device 100 may output an exercise analysis result to analysis information region 1040.

Furthermore, the electronic device 100 may output a start mark 1000a according to a start of an exercise and an end mark 1000b according to an end of the exercise. The first sensor information, for example, may be GPS information on which an information error may due to an environment such as a periphery of a building or the inside thereof as described above.

Figure 11:
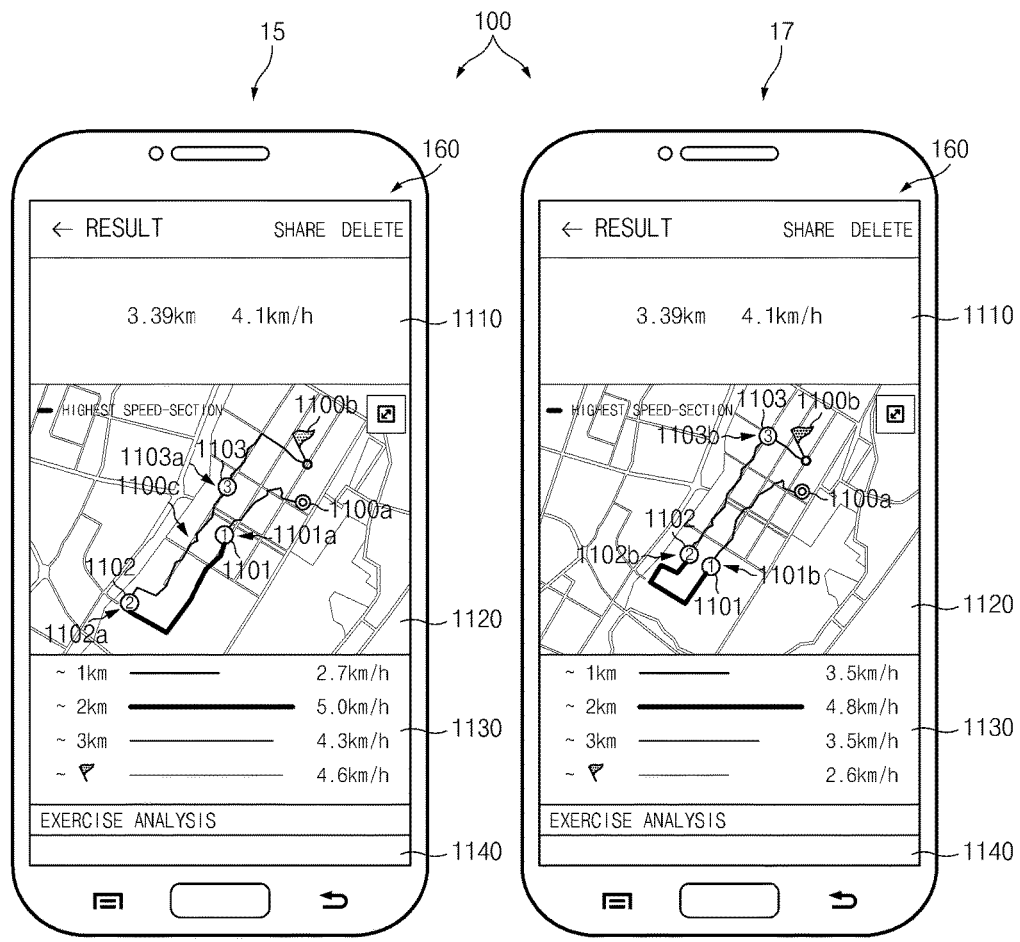
FIG. 11 is a diagram illustrating an example of an exercise performance information display screen according to correction of sensor information according to an embodiment of the present disclosure.

FIG. 11 is a diagram illustrating an example of an exercise performance information display screen according to correction of sensor information according to an embodiment of the present disclosure.

Referring now to FIG. 11, as illustrated in a state 15, the display 160 of the electronic device 100 may output, to a map information region 1120, a route object 1100c according to first sensor information. The electronic device 100 may calculate a reference unit point using first sensor information alone. According to calculated reference unit points, the display 160 of the electronic device 100 may output a first movement mark 1101 to a first position 1101a, may output a second movement mark 1102 to a second position 1102a, and may output a third movement mark 1103 to a third position 1103a. Furthermore, the electronic device 100 may output a start mark 1100a according to a start of an exercise and an end mark 1100b according to an end of the exercise. The first sensor information, for example, may be GPS information on which an information error may due to an environment such as a periphery of a building or the inside thereof. Additionally, the electronic device 100 may output, to a synthetic information region 1110, information such as a total distance traveled 3.39 km and an average moving speed 4.1 km/h. Furthermore, the electronic device 100 may output, to a section information region 1130, information on four sections as illustrated in a state 15. Here, the electronic device 100 may select a moving speed of a second section (1-2 km) as a highest speed based on the first sensor information alone. In addition, the electronic device 100 may output exercise analysis information to an analysis information region 1140.

According to various embodiments of the present disclosure, in the case where the electronic device 100 corrects the first sensor information using second sensor information (e.g., pedometer information), the display 160 may output a screen as illustrated in a state 17. For example, the electronic device 100 may output the first movement mark 1101 to a fourth position 1101b different from the first position 1101a, may output the second movement mark 1102 to a fifth position 1102b different from the second position 1102a, and may output the third movement mark 1103 to a sixth position 1103b different from the third position 1103a. The fifth position 1102b and the sixth position 1103b may be correction positions determined as the first position 1101a is corrected to the fourth position 1101b. According to an embodiment of the present disclosure, a second section (e.g., 1-2 km) between the first movement mark 1101 and the second movement mark 1102 may be a section with a highest moving speed among all sections. The second section with the highest moving speed may be displayed differently from another section (e.g., a 0-1 km section or a 2-3 km section). According to various embodiments of the present disclosure, the electronic device 100 may output a synthetic information region 1110, a section information region 1130, and an analysis information region 1140 in the state 17.

Figure 12:
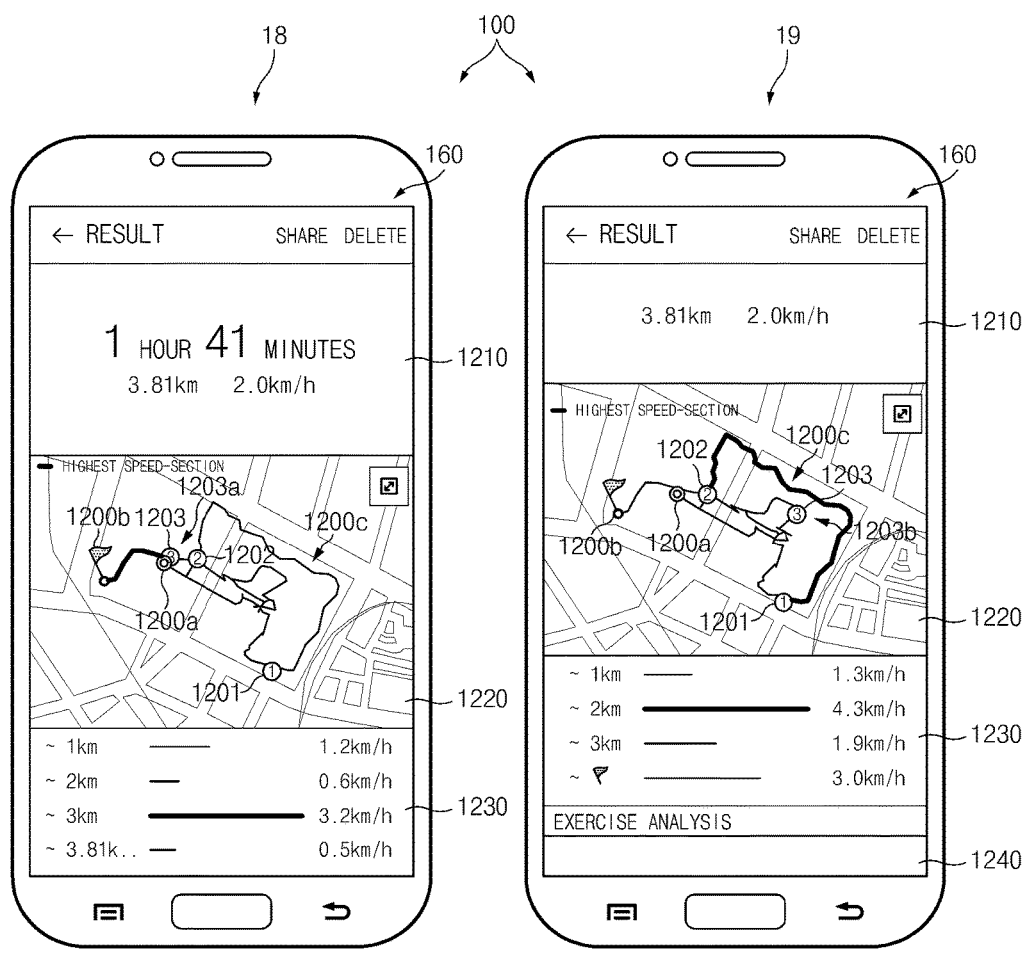
FIG. 12 is a diagram illustrating another example of an exercise performance information display screen according to correction of sensor information according to an embodiment of the present disclosure.

FIG. 12 is a diagram illustrating another example of an exercise performance information display screen according to correction of sensor information according to an embodiment of the present disclosure.

Referring now to FIG. 12, as illustrated in a state 18, the display 160 of the electronic device 100 may output a synthetic information region 1210, a map information region 1220, and a section information region 1230. In addition, the electronic device 100 may output an analysis information region to the display 160 according to an input event such as scrolling or the like. The synthetic information region 1210 may output information such as a total distance traveled 3.81 km and a total exercise time 1 hour and 41 minutes. Furthermore, the electronic device 100 may output, to the section information region 1230, information on four sections. Here, the electronic device 100 may select a third section (e.g., 2-3 km) as a section with a highest speed in comparison with other sections based on the first sensor information alone. In the case where information is displayed using the first sensor information (e.g., GPS information), the display 160 of the electronic device 100 may output a first movement mark 1201 and a second movement mark 1202, and may output a third movement mark 1203 to a first position 1203a as illustrated in a state 18.

According to various embodiments of the present disclosure, in the case where the first sensor information is corrected using second sensor information (e.g., pedometer information), the display 160 of the electronic device 100 may output a screen as illustrated in a state 19. For example, the electronic device 100 may output the first movement mark 1201 and the second movement mark 1202 to the same positions as those of the state 18, and may output the third movement mark 1203 to a second position 1203b unlike the state 18. According to an embodiment of the present disclosure, the electronic device 100 may select a second section (e.g., 1-2 km) between the first movement mark 1201 and the second movement mark 1202 as a section with a highest moving speed among all sections. The second section with the highest moving speed may be displayed differently from another section (e.g., a 0-1 km section or a 2-3 km section). According to various embodiments of the present disclosure, the electronic device 100 may output a synthetic information region 1210, a section information region 1230, and an analysis information region 1240 in the state 19.

As described above, the electronic device 100 may provide more accurate distance information by outputting a movement mark indicating reaching a reference unit point based on a plurality of portions of sensor information. Furthermore, the electronic device 100 may select a highest speed-section from among more correct all sections by determining moving speeds and traveled distances based on the plurality of portions of sensor information.

Figure 13:
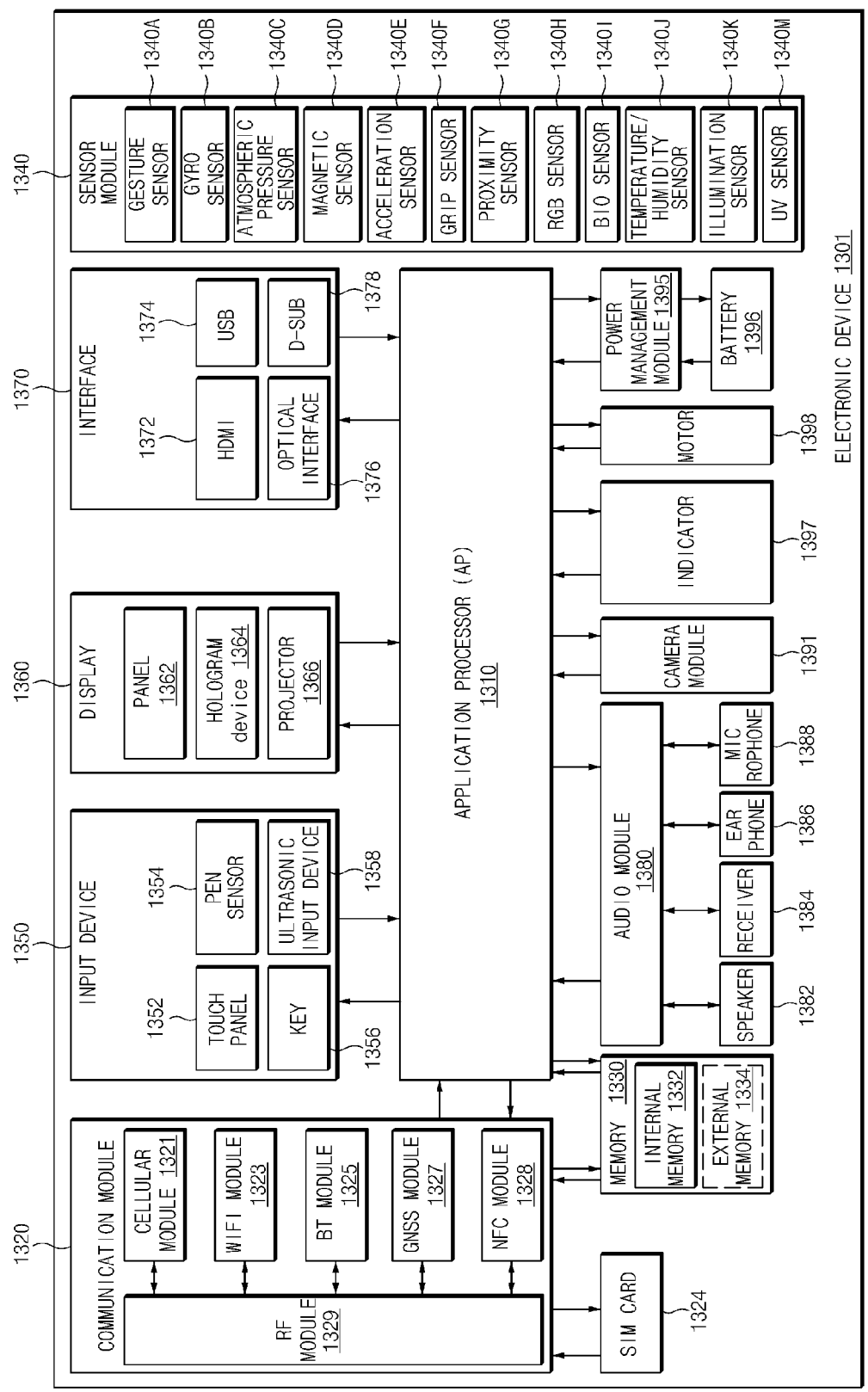
FIG. 13 is a block diagram illustrating an electronic device according to an embodiment of the present disclosure.

FIG. 13 is a block diagram illustrating an electronic device according to an embodiment of the present disclosure.

Referring now to FIG. 13, an electronic device 1301 may include, for example, a part or the entirety of the electronic device described above with respect to the above-mentioned various embodiments of the present disclosure. The electronic device 1301 may include at least one processor (e.g., an application processor (AP)) 1310, a communication module 1320, a subscriber identity module 1324, a memory 1330, a sensor module 1340, an input device 1350, a display 1360, an interface 1370, an audio module 1380, a camera module 1391, a power management module 1395, a battery 1396, an indicator 1397, and a motor 1398.

The at least one processor 1310 may run an operating system or an application program so as to control a plurality of hardware or software elements connected to the processor 1310, and may process various data and perform operations. The processor 1310 may be implemented with, for example, a system on chip (SoC). According to an embodiment of the present disclosure, the processor 1310 may further include a graphic processing unit (GPU) and/or an image signal processor. The processor 1310 may include at least a portion (e.g., the cellular module 1321) of the elements illustrated in FIG. 13. The processor 1310 may load, on a volatile memory, an instruction or data received from at least one of other elements (e.g., a nonvolatile memory) to process the instruction or data, and may store various data in a nonvolatile memory.

The communication module 1320 may have a configuration that is the same as or similar to that of the communication interface 170 of FIG. 1. The communication module 1320 may include, for example, a cellular module 1321, a Wi-Fi module 1323, a Bluetooth module 1325, a GNSS module 1327 (e.g., a GPS module, a GLONASS module, a BeiDou module, or a Galileo module), a near field communication (NFC) module 1328, and a radio frequency (RF) module 1329. In addition, the communication module 1320 may further include an MST module.

The cellular module 1321 may provide, for example, a voice call service, a video call service, a text message service, or an Internet service through a communication network. According to an embodiment of the present disclosure, the cellular module 1321 may identify and authenticate the electronic device 1301 in the communication network using the subscriber identity module 1324 (e.g., a SIM card). According to an embodiment of the present disclosure, the cellular module 1321 may perform at least a part of functions provided by the processor 1310. According to an embodiment of the present disclosure, the cellular module 1321 may include a communication processor (CP).

Each of the Wi-Fi module 1323, the BT module 1325, the GNSS module 1327, and the NFC module 1328 may include, for example, a processor for processing data transmitted/received through the modules. According to some various embodiments of the present disclosure, at least a portion (e.g., at least two) of the cellular module 1321, the Wi-Fi module 1323, the BT module 1325, the GNSS module 1327, and the NFC module 1328 may be included in a single integrated chip (IC) or IC package.

The RF module 1329 may transmit/receive, for example, communication signals (e.g., RF signals). The RF module 1329 may include, for example, a transceiver, a power amp module (PAM), a frequency filter, a low noise amplifier (LNA), an antenna, or the like. According to another embodiment of the present disclosure, at least one of the cellular module 1321, the Wi-Fi module 1323, the BT module 1325, the GNSS module 1327, or the NFC module 1328 may transmit/receive RF signals through a separate RF module.

The subscriber identity module 1324 may include, for example, an embedded SIM and/or a card containing a subscriber identity module, and may include unique identification information (e.g., an integrated circuit card identifier (ICCID)) or subscriber information (e.g., international mobile subscriber identity (IMSI)).

The memory 1330 (e.g., the memory 130) may include an internal memory 1332 or an external memory 1334. The internal memory 1332 may include at least one of a volatile memory (e.g., a dynamic RAM (DRAM), a static RAM (SRAM), a synchronous dynamic RAM (SDRAM), or the like) or a nonvolatile memory (e.g., a one-time programmable ROM (OTPROM), a programmable ROM (PROM), an erasable and programmable ROM (EPROM), an electrically erasable and programmable ROM (EEPROM), a mask ROM, a flash ROM, a flash memory (e.g., a NAND flash memory, a NOR flash memory, or the like), a hard drive, or a solid state drive (SSD)).

The external memory 1334 may include a flash drive, for example, compact flash (CF), secure digital (SD), micro secure digital (Micro-SD), mini secure digital (Mini-SD), extreme digital (xD), multi-media card (MMC), a memory stick, or the like. The external memory 1334 may be operatively and/or physically connected to the electronic device 1301 through various interfaces.

The electronic device may further include a security module. The security module, which is a high-security module compared to the memory 1330, may be a circuit that guarantees secure storage of data and a protected execution environment. The security module may be implemented with a separate circuit, and may include a separate processor. The security module may include, for example, an embedded secure element (eSE) embedded in a fixed chip of the electronic device 1301 or present in a detachable smart chip or secure digital (SD) card. The security module may be driven by an operating system (OS) different from an OS of the electronic device 1301. For example, the security module may be operated based on a Java Card Open Platform (JCOP) operating system.

The sensor module 1340 may, for example, measure physical quantity or detect an operation state of the electronic device 1301 so as to convert measured or detected information into an electrical signal. The sensor module 1340 may include, for example, at least one of a gesture sensor 1340A, a gyro sensor 1340B, a barometric pressure sensor 1340C, a magnetic sensor 1340D, an acceleration sensor 1340E, a grip sensor 1340F, a proximity sensor 1340G, a color sensor 1340H (e.g., a red/green/blue (RGB) sensor), a biometric sensor 1340I, a temperature/humidity sensor 1340J, an illumination sensor 1340K, or an ultraviolet (UV) sensor 1340M. Additionally or alternatively, the sensor module 1340 may include, for example, an olfactory sensor (E-nose sensor), an electromyography (EMG) sensor, an electroencephalogram (EEG) sensor, an electrocardiogram (ECG) sensor, an infrared (IR) sensor, an iris sensor, and/or a fingerprint sensor. The sensor module 1340 may further include a control circuit for controlling at least one sensor included therein. In some various embodiments of the present disclosure, the electronic device 1301 may further include a processor configured to control the sensor module 1340 as a part of the processor 1310 or separately, so that the sensor module 1340 is controlled while the processor 1310 is in a sleep state.

The input device 1350 may include, for example, a touch panel 1352, a (digital) pen sensor 1354, a key 1356, or an ultrasonic input device 1358. The touch panel 1352 may employ at least one of capacitive, resistive, infrared, and ultraviolet sensing methods. The touch panel 1352 may further include a control circuit. The touch panel 1352 may further include a tactile layer so as to provide a haptic feedback to a user.

The (digital) pen sensor 1354 may include, for example, a sheet for recognition which is a part of a touch panel or is separate. The key 1356 may include, for example, a physical button, an optical button, or a keypad. The ultrasonic input device 1358 may sense ultrasonic waves generated by an input tool through a microphone (e.g., a microphone 1388) so as to identify data corresponding to the ultrasonic waves sensed.

The display 1360 (e.g., the display 160) may include a panel 1362, a hologram device 1364, or a projector 1366. The panel 1362 may have a configuration that is the same as or similar to that of the display 160 of FIG. 1. The panel 1362 may be, for example, flexible, transparent, or wearable. The panel 1362 and the touch panel 1352 may be integrated into a single module. The hologram device 1364 may display a stereoscopic image in a space using a light interference phenomenon. The projector 1366 may project light onto a screen so as to display an image. The screen may be disposed in the inside or the outside of the electronic device 1301. According to an embodiment of the present disclosure, the display 1360 may further include a control circuit for controlling the panel 1362, the hologram device 1364, or the projector 1366.

The interface 1370 may include, for example, a high-definition multimedia interface (HDMI) 1372, a universal serial bus (USB) 1374, an optical interface 1376, or a D-subminiature (D-sub) 1378. The interface 1370, for example, may be included in the communication interface 170 illustrated in FIG. 1. Additionally or alternatively, the interface 1370 may include, for example, a mobile high-definition link (MHL) interface, a secure digital (SD) card/multi-media card (MMC) interface, or an infrared data association (IrDA) interface.

The audio module 1380 may convert, for example, a sound into an electrical signal or vice versa. At least a portion of elements of the audio module 1380 may be included in the input/output interface 150 illustrated in FIG. 1. The audio module 1380 may process sound information input or output through a speaker 1382, a receiver 1384, an earphone 1386, or the microphone 1388.

According to an embodiment of the present disclosure, the camera module 1391 for shooting a still image or a video may include, for example, at least one image sensor (e.g., a front sensor or a rear sensor), a lens, an image signal processor (ISP), or a flash (e.g., an LED or a xenon lamp).

The power management module 1395 may manage power of the electronic device 1301. According to an embodiment of the present disclosure, the power management module 1395 may include a power management integrated circuit (PMIC), a charger integrated circuit (IC), or a battery or fuel gauge. The PMIC may employ a wired and/or wireless charging method. The wireless charging method may include, for example, a magnetic resonance method, a magnetic induction method, an electromagnetic method, or the like. An additional circuit for wireless charging, such as a coil loop, a resonant circuit, a rectifier, or the like, may be further included. The battery gauge may measure, for example, a remaining capacity of the battery 1396 and a voltage, current or temperature thereof while the battery is charged. The battery 1396 may include, for example, a rechargeable battery and/or a solar battery.

The indicator 1397 may display a specific state of the electronic device 1301 or a part thereof (e.g., the processor 1310), such as a booting state, a message state, a charging state, or the like. The motor 1398 may convert an electrical signal into a mechanical vibration, and may generate a vibration or haptic effect. Although not illustrated, a processing device (e.g., a GPU) for supporting a mobile TV may be included in the electronic device 1301. The processing device for supporting a mobile TV may process media data according to the standards of digital multimedia broadcasting (DMB), digital video broadcasting (DVB), Media-FLO™, or the like.

Figure 14:
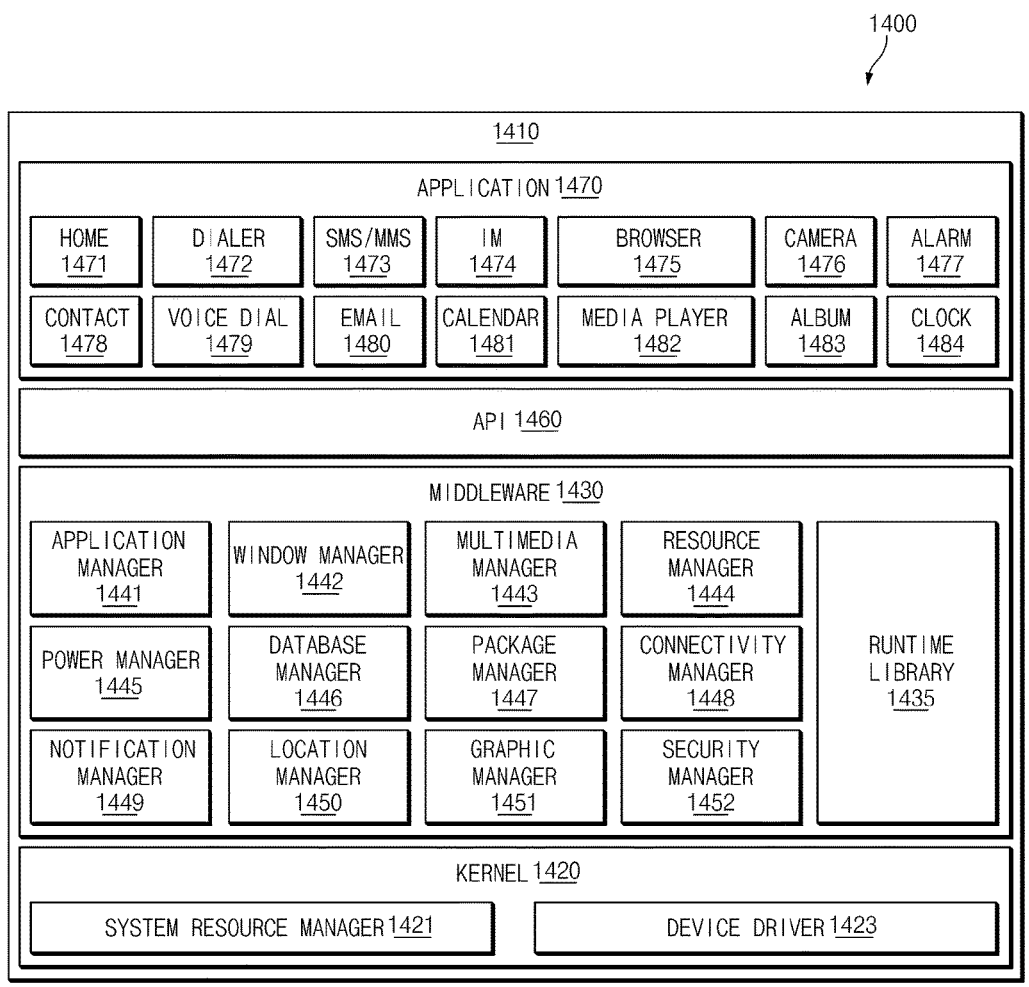
FIG. 14 is a diagram illustrating a program block according to an embodiment of the present disclosure.

FIG. 14 is a diagram illustrating a program block according to an embodiment of the present disclosure.

Referring to FIG. 14, according to various embodiments of the present disclosure, a program module 1410 (e.g., the program 140) may include an operating system (OS) for controlling a resource associated with an electronic device (e.g., the electronic device 100) and/or various applications (e.g., the application program 147) running on the OS. The operating system may be, for example, Android, iOS, Windows, Symbian, Tizen, Bada, or the like.

The program module 1410 may include a kernel 1420, a middleware 1430, an application programming interface (API) 1460, and/or an application 1470. At least a part of the program module 1410 may be preloaded on an electronic device or may be downloaded from an external electronic device (e.g., the electronic device 104 or the server 106).

The kernel 1420 (e.g., the kernel 141) may include, for example, a system resource manager 1421 and/or a device driver 1423. The system resource manager 1421 may perform control, allocation, or retrieval of a system resource. According to an embodiment of the present disclosure, the system resource manager 1421 may include a process management unit, a memory management unit, a file system management unit, or the like. The device driver 1423 may include, for example, a display driver, a camera driver, a Bluetooth driver, a shared memory driver, a USB driver, a keypad driver, a Wi-Fi driver, an audio driver, or an inter-process communication (IPC) driver.

The middleware 1430, for example, may provide a function that the applications 1470 require in common, or may provide various functions to the applications 1470 through the API 1460 so that the applications 1470 may efficiently use limited system resources in the electronic device. According to an embodiment of the present disclosure, the middleware 1430 (e.g., the middleware 145) may include at least one of a runtime library 1455, an application manager 1441, a window manager 1442, a multimedia manager 1443, a resource manager 1444, a power manager 1445, a database manager 1446, a package manager 1447, a connectivity manager 1448, a notification manager 1449, a location manager 1450, a graphic manager 1451, a security manager 1452, or a payment manager.

The runtime library 1435 may include, for example, a library module that a compiler uses to add a new function through a programming language while the application 1470 is running. The runtime library 1435 may perform a function for input/output management, memory management, or an arithmetic function.

The application manager 1441 may mange, for example, a life cycle of at least one of the applications 1470. The window manager 1442 may manage a GUI resource used in a screen. The multimedia manager 1443 may recognize a format required for playing various media files and may encode or decode a media file using a codec matched to the format. The resource manager 1444 may manage a resource such as a source code, a memory, or a storage space of at least one of the applications 1470.

The power manager 1445, for example, may operate together with a basic input/output system (BIOS) to manage a battery or power and may provide power information required for operating the electronic device. The database manager 1446 may generate, search, or modify a database to be used in at least one of the applications 1470. The package manager 1447 may manage installation or update of an application distributed in a package file format.

The connectivity manger 1448 may manage wireless connection of Wi-Fi, Bluetooth, or the like. The notification manager 1449 may display or notify an event such as message arrival, appointments, and proximity alerts in such a manner as not to disturb a user. The location manager 1450 may manage location information of the electronic device. The graphic manager 1451 may manage a graphic effect to be provided to a user or a user interface related thereto. The security manager 1452 may provide various security functions required for system security or user authentication. According to an embodiment of the present disclosure, in the case where an electronic device (e.g., the electronic device 100) includes a phone function, the middleware 1430 may further include a telephony manager for managing a voice or video call function of the electronic device. The payment manager 1454 may relay information for payment from the application 1470 to another application 1470 or the kernel 1420. Furthermore, the payment manager may store, in the electronic device, payment information received from external device, or may transfer information stored therein to the external device.

The middleware 1430 may include a middleware module for forming a combination of various functions of the above-mentioned elements. The middleware 1430 may provide a module specialized for each type of an operating system to provide differentiated functions. Furthermore, the middleware 1430 may delete a part of existing elements or may add new elements dynamically.

The API 1460 (e.g., the API 145) which is, for example, a set of API programming functions, may be provided in different configurations according to an operating system. For example, in the case of Android or iOS, one API set may be provided for each platform, and, in the case of Tizen, at least two API sets may be provided for each platform.

The application 1470 (e.g., the application program 147), for example, may include at least one application for performing functions such as a home 1471, a dialer 1472, an SMS/MMS 1473, an instant message (IM) 1474, a browser 1475, a camera 1476, an alarm 1477, a contact 1478, a voice dial 1479, an e-mail 1480, a calendar 1481, a media player 1482, an album 1483, a clock 1484, a payment, health care (e.g., measure an exercise amount or blood sugar), or environmental information provision (e.g., provide air pressure, humidity, or temperature information).

According to an embodiment of the present disclosure, the application 1470 may include an application (hereinafter referred to as an "information exchange application" for convenience) for supporting information exchange between the electronic device (e.g., the electronic device 100) and an external electronic device (e.g., the electronic device 104). The information exchange application may include, for example, a notification relay application for relaying specific information to the external electronic device or a device management application for managing the external electronic device.

For example, the notification relay application may have a function for relaying, to an external electronic device (e.g., the electronic device 104), notification information generated in another application (e.g., an SMS/MMS application, an e-mail application, a health care application, an environmental information application, or the like) of the electronic device. Furthermore, the notification relay application may receive notification information from the external electronic device and may provide the received notification information to the user.

The device management application, for example, may manage (e.g., install, delete, or update) at least one function (e.g., turn-on/turn off of the external electronic device itself (or some elements) or the brightness (or resolution) adjustment of a display) of the external electronic device (e.g., the electronic device 104) communicating with the electronic device, an application running in the external electronic device, or a service (e.g., a call service or a message service) provided from the external electronic device.

According to an embodiment of the present disclosure, the application 1470 may include a specified application (e.g., a healthcare application of a mobile medical device) according to an attribute of an external electronic device (e.g., the electronic device 104). According to an embodiment of the present disclosure, the application 1470 may include an application received from an external electronic device (e.g., the server 106 or the electronic device 104). According to an embodiment of the present disclosure, the application 1470 may include a preloaded application or a third-party application downloadable from a server. The names of the elements of the program module 1410 illustrated may vary with the type of an operating system.

According to various embodiments of the present disclosure, at least a part of the program module 1410 may be implemented with software, firmware, hardware, or a combination thereof. At least a part of the program module 1410, for example, may be implemented (e.g., executed) by a processor (e.g., the processor 120). At least a part of the program module 1410 may include, for example, a module, a program, a routine, sets of instructions, or a process for performing at least one function.

Each of the elements described herein may be configured with one or more components, and the names of the elements may be changed according to the type of an electronic device. In various embodiments of the present disclosure, an electronic device may include at least one of the elements described herein, and some elements may be omitted or other additional elements may be added. Furthermore, some of the elements of the electronic device according to various embodiments of the present disclosure may be combined with each other so as to form one entity, so that the functions of the elements may be performed in the same manner as before the combination.

The term "module" used herein may represent, for example, a unit including one of hardware, software and firmware or a combination thereof. The term "module" may be interchangeably used with the terms "unit", "logic", "logical block", "component" and "circuit". The "module" may be a minimum unit of an integrated component or may be a part thereof. The "module" may be a minimum unit for performing one or more functions or a part thereof. The "module" may be implemented mechanically or electronically. For example, the "module" may include at least one of an application-specific integrated circuit (ASIC) chip, a field-programmable gate array (FPGA), and a programmable-logic device for performing some operations, which are known or will be developed.

At least a part of devices (e.g., modules or functions thereof) or methods (e.g., operations) according to various embodiments of the present disclosure may be implemented as instructions stored in a computer-readable storage medium in the form of a program module. In the case where the instructions are performed by a processor (e.g., the processor 120), the processor may perform functions corresponding to the instructions. The computer-readable storage medium may be, for example, the memory 130.

The apparatuses and methods of the disclosure can be implemented in hardware, and in part as firmware or via the execution of software or computer code in conjunction with hardware that is stored on a non-transitory machine readable medium such as a CD ROM, a RAM, a floppy disk, a hard disk, or a magneto-optical disk, or computer code downloaded over a network originally stored on a remote recording medium or a non-transitory machine readable medium and stored on a local non-transitory recording medium for execution by hardware such as a processor, so that the methods described herein are loaded into hardware such as a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc., that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. In addition, an artisan understands and appreciates that a "processor", "microprocessor", "controller", or "control unit" constitute hardware in the disclosure and appended claims that contain circuitry that is configured for operation. Under the broadest reasonable interpretation, the appended claims constitute statutory subject matter in compliance with 35 U.S.C. § 101 and none of the elements are software per se. The term "module" as used in this application refers to the attachable structure of portions of the housing, and such components comprise statutory subject matter.

The definition of the term "unit" as referred to herein are to be understood as constituting hardware circuitry such as a CCD, CMOS, SoC, AISC, FPGA, a processor or microprocessor (a controller) configured for a certain desired functionality, or a communication module containing hardware such as transmitter, receiver or transceiver, or a non-transitory medium comprising machine executable code that is loaded into and executed by hardware for operation, in accordance with statutory subject matter under 35 U.S.C. § 101 and do not constitute software per se.

The computer-readable storage medium may include a hard disk, a floppy disk, a magnetic medium (e.g., a magnetic tape), an optical medium (e.g., a compact disk read only memory (CD-ROM) and a digital versatile disc (DVD)), a magneto-optical medium (e.g., a floptical disk), or a hardware device (e.g., a read only memory (ROM), a random access memory (RAM), or a flash memory). The program instructions may include machine language codes generated by compilers and high-level language codes that can be executed by computers using interpreters. The above-mentioned hardware device may be configured to be operated as one software module for performing operations of various embodiments of the present disclosure and vice versa.

A module or a program module according to various embodiments of the present disclosure may include at least one of the above-mentioned elements, or some elements may be omitted or other additional elements may be added. Operations performed by the module, the program module or other elements according to various embodiments of the present disclosure may be performed in a sequential, parallel, iterative or heuristic way. Furthermore, some operations may be performed in another order or may be omitted, or other operations may be added.

According to various embodiments of the present disclosure, functions may be performed more accurately based on various sensor information.

The above embodiments of the present disclosure are illustrative and not limitative. Various alternatives and equivalents are possible. Other additions, subtractions, or modifications are obvious in view of the present disclosure and are intended to fall within the scope of the appended claims.

What is claimed is:

1. An electronic device comprising:
 a non-transitory memory configured to store one or more executable instructions associated with an exercise function;
 at least one processor operatively connected to the memory, the at least one processor executes at least one instruction associated with the exercise function to output information associated with the exercise function;
 a plurality of sensors for detecting a present location or movements of the electronic device; and
 a display operatively coupled to the at least one processor,
 wherein execution of at least one instruction configures the at least one processor to:
 calculate a distance traveled by the electronic device based on sensing information received from the plurality of sensors configured to collect sensing information in response to detecting movement of the electronic device, and when the traveled distance matches a predetermined distance to at least one reference unit point, detect whether location information is available from a first sensor of the plurality of sensors,
wherein when the location information is available from the first sensor, a specified object is displayed along a displayed route to mark traversal of the predetermined distance, and when the location information is unavailable from the first sensor, the specified object is not displayed along the displayed route.

2. The electronic device of claim 1, wherein the execution of the at least one instruction configures the at least one processor to:
obtain time information associated with a distance traveled information adjacent to the at least one reference unit point or time information corresponding to the at least one reference unit point based on the sensing information obtained received from the plurality of sensors, and
select a screen portion of the display showing GPS coordinate information corresponding to the time information, or showing GPS coordinate information of a specified time within a predetermined time period of the time information as a position to which the object is to be output.

3. The electronic device of claim 1, wherein the plurality of sensors includes a GPS sensor and a pedometer,
wherein when the location information is unavailable from the first sensor and the specified object is not displayed, a second object different from the specified object is displayed along a corresponding section of the displayed route.

4. The electronic device of claim 1, wherein the execution of the at least one instruction configures the at least one processor to output a route object corresponding to a total distance traveled based on GPS information from among a portion of sensing information, or output, to a screen, a mark indicating the reference unit point.

5. The electronic device of claim 1, wherein the execution of the at least one instruction configures the at least one processor to output to at least one screen portion of a display an object having order information corresponding to the at least one reference unit point.

6. The electronic device of claim 1, wherein the execution of the at least one instruction configures the at least one processor to display a certain screen region including the at least one reference unit point differently from a peripheral region of the certain screen region when the plurality of sensing information corresponding to the reference unit point does not exist.

7. The electronic device of claim 6, wherein execution of the at least one instruction configures the at least processor to configure a display of the certain screen region including the at least one reference unit point so that the certain screen region differs in at least one of a line number, width, or color from the peripheral region of the certain screen region.

8. The electronic device of claim 1, wherein the execution of the at least one instruction configures the at least one processor to output to a screen portion of the display an object corresponding to the at least one reference unit point corresponding to a sensing information location collected immediately before the reference unit point in a case where the sensing information corresponding to the reference unit point and exercise end sensing information are equal in location.

9. The electronic device of claim 1, wherein the execution of the at least one instruction configures the at least one processor to calculate a moving speed based on the plurality of sensing information, and perform a screen display for a section with a highest speed among sections divided for each at least one reference unit point differently from the screen display for adjacent sections.

10. The electronic device of claim 1, wherein the execution of the at least one instruction configures the at least one processor to perform to perform screen display for a position for which a portion of the sensing information does not exist differently from the screen display for another section.

11. A using method in an electronic device, the method comprising:
collecting at least a portion of sensing information using at least one of a plurality of sensors detecting movement or a present location of the electronic device;
calculating, by a processor, a distance traveled based on the at least a portion of collected sensing information; and
when the traveled distance matches a predetermined distance to at least one reference unit point, detecting whether location information is available from a first sensor of the plurality of sensors,
wherein when the location information is available from the first sensor a specified object is displayed along a displayed route to mark traversal of the predetermined distance, and when the location information is unavailable from the first sensor, the specified object is not displayed along the displayed route.

12. The sensing information using method of claim 11, comprising:
obtaining time information of distance traveled information adjacent to the reference unit point, or corresponding to the reference unit point, based on the collected sensing information; and
selecting a screen portion corresponding to GPS coordinate information corresponding to the time information, or showing GPS coordinate information of a specified time within a predetermined time period of the time information as a position to which the object is to be output.

13. The sensing information using method of claim 11, wherein the plurality of sensors includes a GPS sensor and a pedometer,
wherein when the location information is unavailable from the first sensor and the specified object is not displayed, a second object different from the specified object is displayed along a corresponding section of the displayed route.

14. The sensing information using method of claim 11, further comprising:
outputting a route object corresponding to a total distance traveled based on GPS information among the collected portion of sensing information; and
outputting, to a screen, a mark indicating the reference unit point.

15. The sensing information using method of claim 11, wherein displaying the specified object includes order information that is output to at least one screen portion corresponding to the at least one reference unit point.

16. The sensing information using method of claim 11, wherein displaying the specified object further comprises:
displaying a certain screen region including the reference unit point differently from a periphery of the certain screen region when sensing information corresponding to the reference unit point does not exist.

17. The sensing information using method of claim 16, wherein the displaying of the certain screen region corresponding to the reference unit point so that the certain screen region differs in at least one of a line number, width, or color from the periphery of the certain screen region.

18. The sensing information using method of claim 11, wherein displaying the specified object further comprises outputting an object corresponding to the reference unit point to a screen portion corresponding to a sensing information location collected immediately before the reference unit point in a case where the sensing information of the reference unit point and exercise end sensing information are in a same location.

19. The sensing information using method of claim 11, wherein displaying the specified object further comprises calculating a moving speed based on the portions of sensing information and performing screen display for a section with a highest speed among sections divided for each reference unit point differently from the screen display for adjacent sections.

20. The sensing information using method of claim 11, wherein displaying the specified object comprises displaying on a display a position for which a portion of the sensing information does not exist differently from screen display for another section.

\* \* \* \* \*